United States Patent
Jain et al.

(10) Patent No.: US 6,666,862 B2
(45) Date of Patent: Dec. 23, 2003

(54) RADIO FREQUENCY ABLATION SYSTEM AND METHOD LINKING ENERGY DELIVERY WITH FLUID FLOW

(75) Inventors: Mudit K. Jain, Woodbury, MN (US); Milton M. Morris, Minneapolis, MN (US); Bruce KenKnight, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 144 days.

(21) Appl. No.: 09/797,435

(22) Filed: Mar. 1, 2001

(65) Prior Publication Data

US 2002/0169445 A1 Nov. 14, 2002

(51) Int. Cl.$^7$ .............................................. A61B 18/18
(52) U.S. Cl. ........................ 606/41; 606/34; 607/101; 607/102
(58) Field of Search .............................. 606/32, 34, 35, 606/38, 41, 46, 48–51; 607/101–102, 122

(56) References Cited

U.S. PATENT DOCUMENTS

| | | | |
|---|---|---|---|
| 6,049,737 A | | 4/2000 | Simpson et al. |
| 6,197,023 B1 | * | 3/2001 | Muntermann ................ 606/41 |
| 6,440,129 B1 | * | 8/2002 | Simpson ..................... 606/42 |
| 2001/0002000 A1 | | 5/2001 | Kumar et al. |
| 2002/0002372 A1 | | 1/2002 | Jahns et al. |

FOREIGN PATENT DOCUMENTS

| | | |
|---|---|---|
| WO | WO 96/36282 | 11/1996 |
| WO | WO 97/17014 | 5/1997 |
| WO | WO 00/51511 | 9/2000 |
| WO | WO 00/51513 | 9/2000 |

OTHER PUBLICATIONS

Helen Høgh Petersen, MD et al, "Lesion Dimensions During Temperature–Controlled Radiofrequency Catheter Ablaton of Left Ventricular Porcine Myocardium", Circulation Journal of the american heart Association, vol. 99, No. 2, Jan. 19, 1999, pp 319–325,; USA.
David E. Haines, "The Biophysics of Radiofrequency Catheter Ablation in the Heart: The Importance of Temperature Monitoring;," Pacing And Clinical Electrophysiology, Mar. 1993, vol. 16, No. 3, Part II, pp 586–591; Futura Publishing Company, Inc., Mt. Kisco, NY.
David E. Haines et al., "Tissue Heating During Radiofrequency Catheter Ablation: A Thermodynamic Model and Observations in Isolated Perfused and Superfused Canine Right Ventricular Free Wall," Pacing And Clinical Eletrophysicology, Jun. 1989, vol. 12, No. 6, pp 962–976; Futura Publishing Company, Inc., Mt. Kisco, NY.
Mudit K. Jain, "An Experimental and Numerical Analysis of the Spatiotemporal Behavior of Radiofrequency Ablation," Department of biomedical Engineering, Duke University, UMI Microform #9942512, (1999) UMI Company, Ann Arbor, MI.

* cited by examiner

Primary Examiner—Linda C. M. Dvorak
Assistant Examiner—David M. Ruddy
(74) Attorney, Agent, or Firm—Fulwider Patton Lee & Utecht, LLP

(57) ABSTRACT

Information indicative of the flow rate of fluid through a biological organ is provided to a processor. Using this information the processor assesses whether the fluid-flow rate is high or low and controls a generator such that the generator provides energy to an electrode positioned within the organ to effect tissue ablation. Energy of a first level is provided during periods of high fluid-flow and energy of a second level, less than the first level, during periods of low fluid-flow. The flow rate information may be provided by an electrocardiograph (ECG) device or a flow sensor. A temperature sensor provides temperature signals to the processor indicative of the electrode temperature. The processor further controls the generator based on the electrode temperature to maintain the temperature at or near a target temperature and below a maximum threshold temperature.

44 Claims, 24 Drawing Sheets

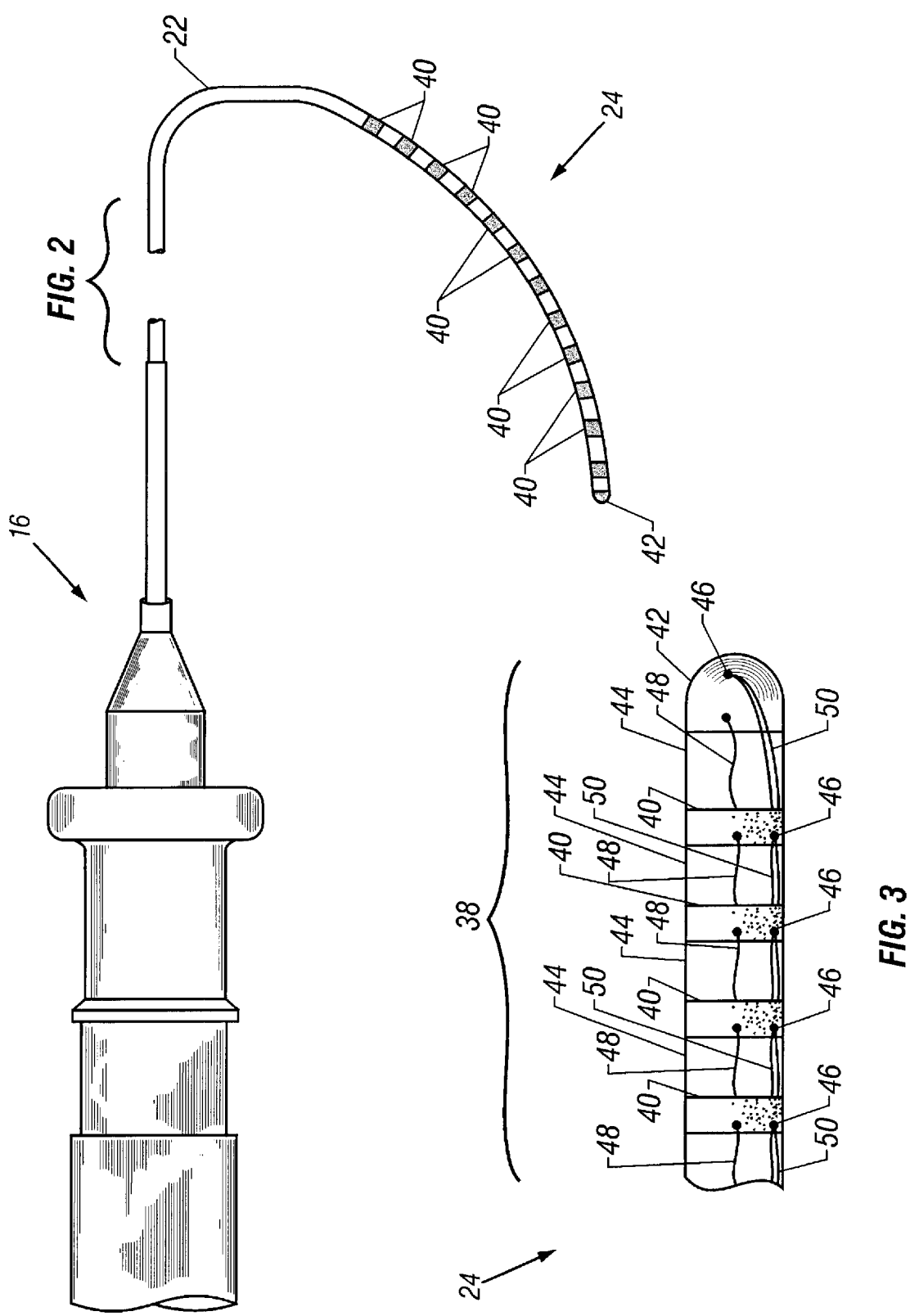

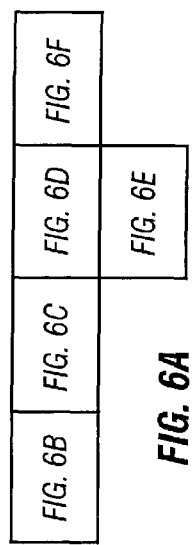
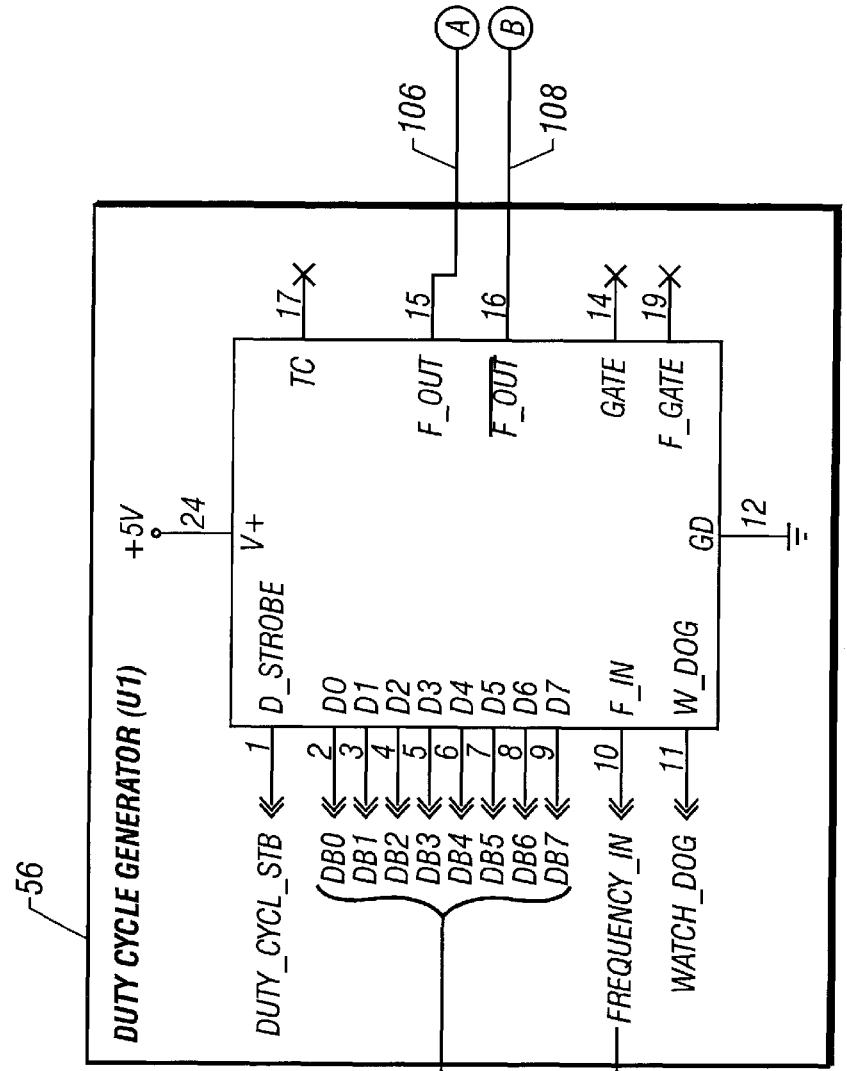
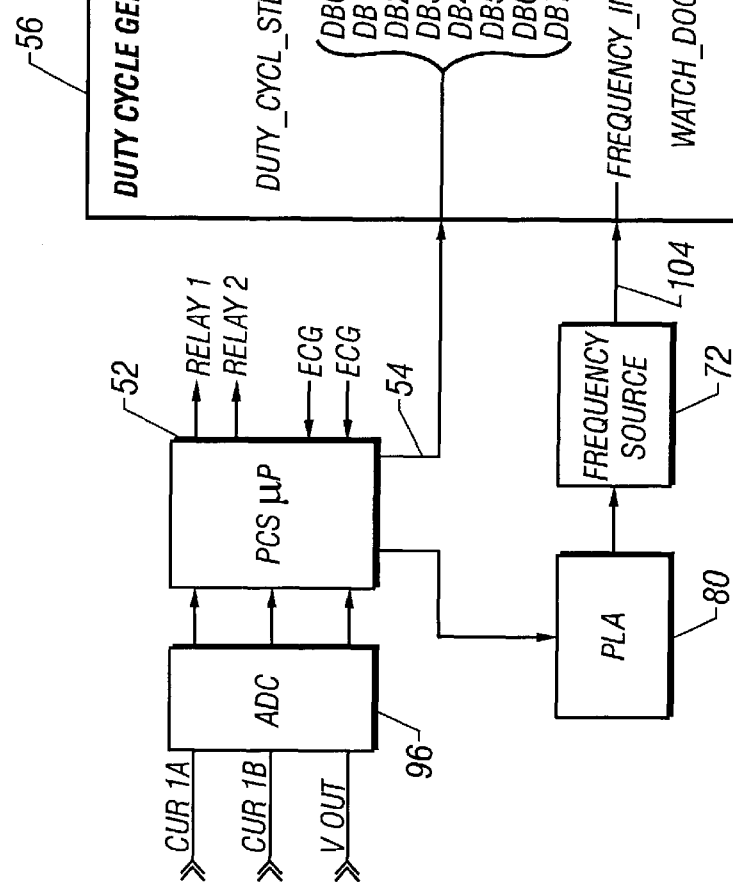
FIG. 6A
FIG. 6B

RADIO FREQUENCY ABLATION SYSTEM AND METHOD LINKING ENERGY DELIVERY WITH FLUID FLOW

BACKGROUND OF THE INVENTION

The invention relates generally to an electrophysiological ("EP") system and method for providing energy to biological tissue within a biological site, and more particularly, to an EP system and method for controlling the delivery of RF energy to the tissue based on the flow of fluid through the biological site.

The heart beat in a healthy human is controlled by the sinoatrial node ("S-A node") located in the wall of the right atrium. The S-A node generates electrical signal potentials that are transmitted through pathways of conductive heart tissue in the atrium to the atrioventricular node ("A-V node") which in turn transmits the electrical signals throughout the ventricle by means of the His and Purkinje conductive tissues. Improper growth of, or damage to, the conductive tissue in the heart can interfere with the passage of regular electrical signals from the S-A and A-V nodes. Electrical signal irregularities resulting from such interference can disturb the normal rhythm of the heart and cause an abnormal rhythmic condition referred to as "cardiac arrhythmia."

While there are different treatments for cardiac arrhythmia, including the application of anti-arrhythmia drugs, in many cases ablation of the damaged tissue can restore the correct operation of the heart. Such ablation can be performed by percutaneous ablation, a procedure in which a catheter is percutaneously introduced into the patient and directed through an artery to the atrium or ventricle of the heart to perform single or multiple diagnostic, therapeutic, and/or surgical procedures. In such case, an ablation procedure is used to destroy the tissue causing the arrhythmia in an attempt to remove the electrical signal irregularities or create a conductive tissue block to restore normal heart beat or at least an improved heart beat. Successful ablation of the conductive tissue at the arrhythmia initiation site usually terminates the arrhythmia or at least moderates the heart rhythm to acceptable levels. A widely accepted treatment for arrhythmia involves the application of RF energy to the conductive tissue.

In the case of atrial fibrillation ("AF"), a procedure published by Cox et al. and known as the "Maze procedure" involves continuous atrial incisions to prevent atrial reentry and to allow sinus impulses to activate the entire myocardium. While this procedure has been found to be successful, it involves an intensely invasive approach. It is more desirable to accomplish the same result as the Maze procedure by use of a less invasive approach, such as through the use of an appropriate EP catheter system providing RF ablation therapy. In this therapy, transmural ablation lesions are formed in the atria to prevent atrial reentry and to allow sinus impulses to activate the entire myocardium.

During ablation, electrodes carried by an EP catheter are placed in intimate contact with the target endocardial tissue. RF energy is applied to the electrodes to raise the temperature of the target tissue to a non-viable state. In general, the temperature boundary between viable and non-viable tissue is approximately 48° Centigrade. Tissue heated to a temperature above 48° C. becomes non-viable and defines the ablation volume. The objective is to elevate the tissue temperature, which is generally at 37° C., fairly uniformly to an ablation temperature above 48° C., while keeping both the temperature at the tissue surface and the temperature of the electrode below 100° C. When the blood temperature reaches approximately 100° C., coagulum generally occurs.

Blood coagulation is a major limitation/complication associated with RF ablation therapy. Coagulation can lead to thromboembolism and also form an insulating layer around the electrode hindering further energy delivery required for ablation therapy. Thus, heating of blood is a major concern for ablation safety and efficacy. During ablation therapy, it is known that the temperature of blood near an electrode is dependent on the blood flow rate. Low blood flow results in reduced convective heat dissipation within the blood pool around the electrode and thus higher blood temperature. Conversely, high blood flow rate results in increased convective heat dissipation within the blood pool around the electrode and thus a lower blood temperature.

Conventional RF ablation systems fail to account for the effect that varying blood flow rates have on blood, electrode and tissue temperatures, which can be substantial. During an ablation procedure, conventional systems apply a level of RF energy to the electrodes sufficient to elevate the tissue temperature to a level that causes the tissue to become non-viable. The level of RF energy is generally constant regardless of the blood flow rate and is only adjusted if the system employs some type of temperature feedback control. In these systems an attempt is made to guard against blood coagulation and coagulum formation by monitoring the temperature of the electrodes, usually using a thermocouple attached to the electrode. When a threshold temperature is reached, the application of RF energy is either reduced or shut off. However, such thermocouples are generally located at the tissue/electrode contact location, which can have a significantly different temperature than the opposite side of the electrode that is in the blood pool.

Such systems tend either to have a high incidence of coagulation or to operate inefficiently. Coagulation is likely to occur in these systems when the RF energy delivered to the electrode is set to an ablation-inducing level during periods of high-blood flow. The temperature sensing thermocouple does not provide the system with sufficient information about the temperature of the blood pool. Consequently, the convective heat dissipation effect of the high-blood flow keeps the blood pool around the electrode cool and ablation is efficiently accomplished, however, during periods of low-blood flow, the reduced convective heat dissipation allows the blood pool to heat. Over the course of an ablation procedure, the cumulative effect of the periods of low-blood flow is likely to result in coagulum formation.

In order to avoid coagulation the energy level may be reduced. This, however, tends to lead to an inefficient ablation procedure. If the energy level is set to induce ablation during periods of low flow, the convective heat dissipation effect during periods of high-blood flow reduces the electrode temperature and thus the tissue temperature to a non-ablative level. The culmination of these periods of non-ablative temperature levels at best increases the amount of time necessary to achieve an ablation-inducing temperature and thus the overall procedure time, and at worst prevents the electrode from ever reaching an ablation-inducing level.

Hence, those skilled in the art have recognized a need for a RF ablation system and method that controls and adjusts the RF energy level delivered to tissue within a biological site based on the flow rate of fluid through the site. The invention fulfills this need and others.

SUMMARY OF THE INVENTION

Briefly and in general terms, the present invention is directed to a system for, and a method of, controlling the delivery of energy to biological tissue during an ablation procedure based on the flow of fluid through the biological site.

In one aspect, the invention relates to a system for applying energy to biological tissue within a biological organ having fluid flowing therethrough. The system includes a generator for providing energy and a catheter carrying an electrode system at its distal end. The distal end of the catheter is adapted to be positioned in a biological organ and the electrode system is adapted to receive energy from the generator. The system further includes a device adapted to provide flow rate information indicative of the flow rate of the fluid through the biological organ and a processor adapted to receive the flow rate information. The processor is adapted to assess whether the fluid-flow rate is high or low and control the generator such that the generator provides energy of a first level to the electrode during periods of high fluid-flow and energy of a second level, less than the first level, during periods of low fluid-flow.

By providing a processor that controls a generator such that energy of a first level is applied during periods of high fluid-flow and energy of a second level, less than the first level is applied during periods of low fluid-flow, the system is able to dynamically control the application of energy to the electrode based on the rate of fluid flow through the biological site. In linking the applied energy level to the fluid-flow rate, the system accounts for the effect that varying fluid-flow rates have on blood, electrode and tissue temperatures and maintains the electrode at or near an ablative temperature throughout an ablation procedure, thereby increasing ablation efficiency and reducing chances of blood coagulation.

In a detailed aspect of the invention, the processor controls the generator to increase the energy level to the first energy level at the beginning of the high flow period and to decrease the energy level to the second energy level toward the end of the high flow period and before the beginning of the next low flow period. In another detailed facet, the system further includes a temperature sensor for providing temperature signals to the processor. The signals are indicative of the temperature at the electrode system. In this facet, the processor is adapted to determine the temperature at the electrode system based on the temperature signals and to control the generator such that the level of energy applied to the electrode system maintains the temperature of the electrode system at or near a target temperature. In a further detailed aspect, the processor is adapted to adjust the level of energy output by the generator during a subsequent low/high period based on the temperature of the electrode system during the previous low/high period. In another detailed aspect, the system further includes a temperature sensor for providing temperature signals to the processor. The signals are indicative of the temperature at the electrode system. In this aspect, the processor is adapted to determine the temperature at the electrode system and to control the generator such that the level of energy applied to the electrode system maintains the temperature of the electrode system below a maximum threshold temperature.

In another detailed aspect of the invention, the flow rate information device includes an electrocardiograph (ECG) device adapted to monitor changes in electrical activity and the flow rate information includes ECG signals. In a further detailed aspect, the ECG device includes either one or both of an internal ECG sensor and an external ECG sensor. In another further detailed aspect, the ECG device includes at least one ECG filter in electrical communication with the electrode system. The ECG filter receives electrical signals from the electrode system and outputs them as ECG signals. For an ECG signal providing a waveform having a sequence of alternating P waves and T waves, the processor is adapted to identify the periods between a P wave and its subsequent T wave as high fluid-flow periods and the periods between a T wave and the next P wave as low fluid-flow periods. For an ECG signal providing a waveform having a sequence of alternating QRS complex waves and T waves, the processor is adapted to identify the periods between the onset of a QRS complex wave and the subsequent T wave as high fluid-flow periods and the periods between a T wave and the next QRS complex wave as low flow periods.

In another detailed aspect of the invention, the flow rate information device includes at least one flow sensor located near the electrode system that is adapted to sense fluid flow and the flow rate information includes velocity values. In a further detailed aspect, the processor is adapted to identify periods during which the sensor signals provide a velocity value greater than or equal to a predetermined velocity value as high fluid-flow periods and those periods during which the velocity value is less than the predetermined velocity value as low fluid-flow periods.

In another aspect, the invention relates to a method of applying energy to biological tissue within a biological organ. The method includes the steps of positioning an electrode within the biological organ, such that a portion of the electrode contacts the biological tissue and determining the biological fluid-flow rate within the biological organ. The method further includes the steps of, during periods of high biological fluid flow, applying energy of a first level to the biological tissue and during periods of low biological fluid flow, reducing the level of energy applied to a second level, less than the first level.

In a detailed aspect of the invention, the first level of energy is substantially constant and the second level of energy is substantially zero. In another detailed aspect, the steps of applying energy of a first level and reducing the level of energy to a second level includes the steps of increasing the energy to the first energy level at the beginning of a high flow period and decreasing the energy level to the second energy level toward the end of the high flow period and before the low flow period.

In another detailed aspect of the invention, the method further includes the steps of monitoring the temperature of the electrode and adjusting the level of energy applied to the electrode to maintain the temperature of the electrode at or near a target temperature. In a further detailed facet, the method further includes the step of, for a sequence of alternating high flow rate periods and low flow rate periods, adjusting the level of energy during a subsequent low/high period based on the temperature of the electrode during the previous low/high period.

In another detailed facet of the invention, the step of determining the biological fluid-flow rate includes the steps of measuring changes in voltage occurring in the human body with each heart beat to produce an electrocardiogram waveform having a sequence of alternating P waves and T waves and identifying high fluid-flow periods as those periods between a P wave and its subsequent T wave and low fluid-flow periods are those periods between a T wave and the next P wave. In another detailed aspect, the step of determining the biological fluid-flow rate includes the steps of measuring changes in voltage occurring in the human body with each heart beat to produce an electrocardiogram waveform having a sequence of alternating QRS complex waves and T waves and identifying high fluid-flow periods as those periods between the onset of a QRS complex wave and the subsequent T wave and low fluid-flow periods are those periods between a T wave and the next QRS complex wave. In yet another detailed aspect, the step of determining the biological fluid-flow rate includes the steps of measuring the velocity of the fluid flow and identifying those periods during which the sensor signals provide a velocity value greater than or equal to a predetermined velocity value as high fluid-flow periods and those periods during which the velocity value is less than the predetermined velocity value as low fluid-flow periods.

In another aspect, the invention relates to a system for applying energy to biological tissue within a biological organ having fluid flowing therethrough. The system includes a generator for providing energy and a catheter carrying an electrode system at its distal end. The distal end is adapted to be positioned in a biological organ and the electrode system is adapted to receive energy from the generator. The system further includes a device adapted to provide flow rate information indicative of the flow rate of the fluid through the biological organ and a processor adapted to control the generator such that the generator provides energy to the electrode system based on the flow rate information.

In a detailed aspect of the invention, a preset flow rate and a maximum energy level are programmed into the processor and the processor is adapted to compare the measured flow rate to the preset flow rate. When the measured flow rate is greater than or equal to the preset flow rate, the processor sets the provided energy level to the maximum energy level. When the measured flow rate is less than the preset flow rate, the processor determines the rate of reduction of the measured flow rate relative to the preset flow rate and sets the provided energy level to a value less than the maximum energy level. The provided level is a multiple of the maximum energy level and the multiple is set based on the determined reduction rate.

In another detailed aspect of the invention, a preset flow rate, a high target temperature, and a low target temperature are programmed into the processor. The processor is adapted to monitor the temperature of the electrode and compare the measured flow rate to the preset flow rate. When the measured flow rate is greater than or equal to the preset flow rate, the processor determines the rate of increase of the measured flow rate relative to the preset flow rate and sets the applied energy level to a value greater than the current energy level, the applied level being a multiple of the current energy level and the multiple being set based on the determined increase rate. The processor also compares the electrode temperature to the high target temperature and adjusts the applied energy level to maintain the electrode temperature near the high target temperature. When the measured flow rate is less than or equal to the preset flow rate, the processor determines the rate of reduction of the measured flow rate relative to the preset flow rate and sets the applied energy level to a value less than the current energy level, the applied level being a multiple of the current energy level, the multiple being set based on the determined reduction rate. The processor also compares the electrode temperature to the low target temperature and adjusts the applied energy level to maintain the electrode temperature near the low target temperature.

In another facet, the invention relates to a method of ablating biological tissue within a biological organ having biological fluid flowing therethrough. The method includes the step of positioning an electrode within the biological organ such that a portion of the electrode contacts the biological tissue. The method further includes the steps of measuring the biological fluid-flow rate within the biological organ and applying energy to the electrode based on the flow rate measurement.

In a detailed aspect of the invention, the step of measuring the biological fluid-flow rate includes the steps of positioning a flow sensor within the biological fluid and determining the flow rate of the biological fluid. In a further detailed facet, the step of applying energy to the electrode based on the flow rate measurement includes the steps of establishing a preset flow rate and a maximum energy level and comparing the measured flow rate to the preset flow rate. The method further includes the step of, when the measured flow rate is greater than or equal to the preset flow rate, setting the applied energy level to the maximum energy level. When the measured flow rate is less than the preset flow rate, the method includes the steps of determining the rate of reduction of the measured flow rate relative to the preset flow rate and setting the applied energy level to a value less than the maximum energy level, the applied level being a multiple of the maximum energy level, the multiple being set based on the determined reduction rate.

In another detailed aspect of the invention, the method further includes the steps of monitoring the temperature of the electrode and adjusting the level of energy applied to the electrode to maintain the temperature of the electrode at or near a target temperature. In a further detailed aspect, the steps of applying energy to the electrode based on the flow rate measurement and adjusting the level of energy applied to the electrode to maintain the temperature of the electrode at or near a target temperature includes the steps of establishing a high target temperature, a low target temperature and a preset flow rate value, monitoring the temperature of the electrode and comparing the measured flow rate to the preset flow rate. When the measured flow rate is greater than or equal to the preset flow rate, the method includes the further steps of determining the rate of increase of the measured flow rate, setting the applied energy level to a value greater than the current energy level, the applied level being a multiple of the current energy level, the multiple being set based on the determined increase rate. Also included are the steps of comparing the electrode temperature to the high target temperature and adjusting the applied energy level to maintain the electrode temperature near the high target temperature. When the measured flow rate is less than or equal to the preset flow rate, the method includes the further steps of determining the rate of reduction of the measured flow rate, setting the applied energy level to a value less than the current energy level, the applied level being a multiple of the current energy level, the multiple being set based on the determined reduction rate. Also included are the steps of comparing the electrode temperature to the low target temperature and adjusting the applied energy level to maintain the electrode temperature near the low target temperature.

In another aspect, the invention relates to a system for applying energy to biological tissue within a biological subject having fluid flowing therethrough. The system includes a generator for providing energy and a catheter carrying an electrode system. The catheter is adapted to be positioned in a biological organ and the electrode system adapted to receive energy from the generator. The system further includes a device adapted to provide flow rate information indicative of the flow rate of the fluid through the biological subject and a processor adapted to control the generator such that the generator provides energy to the electrode system based on the flow rate information.

These and other aspects and advantages of the invention will become apparent from the following detailed description and the accompanying drawings which illustrate by way of example the features of the invention.

BRIEF DESCRIPTION OF THE DRAWINGS

FIG. 2 is a diagram of the catheter system of FIG. 1 presenting more detail that includes a handle and a catheter sheath having a preformed distal segment carrying a linear array of electrodes;

FIG. 3 is a detailed schematic block diagram of a portion of the distal segment of the catheter system of FIG. 2, depicting a tip electrode and several band electrodes;

FIGS. 5-1 and 5-2 form a block diagram of a multi-channel ablation system configured in accordance with the configuration of FIGS. 4A and 4B wherein a single PCS microprocessor controls the application of ablation energy to each channel individually based in part on fluid-flow rate information provided by a plurality of ECG devices;

FIGS. 6A, 6B, 6C, 6D, 6E and 6F form a schematic diagram of an embodiment of a PCS including ECG devices, with FIG. 6A showing how FIGS. 6B, 6C, 6D, 6E and 6F are related;

FIGS. 13-1 and 13-2 form a block diagram presenting a detailed configuration of another embodiment of the ablation system of FIG. 1 wherein the fluid-flow rate information is obtained using a flow sensor;

DETAILED DESCRIPTION OF PREFERRED EMBODIMENTS

Figure 1:
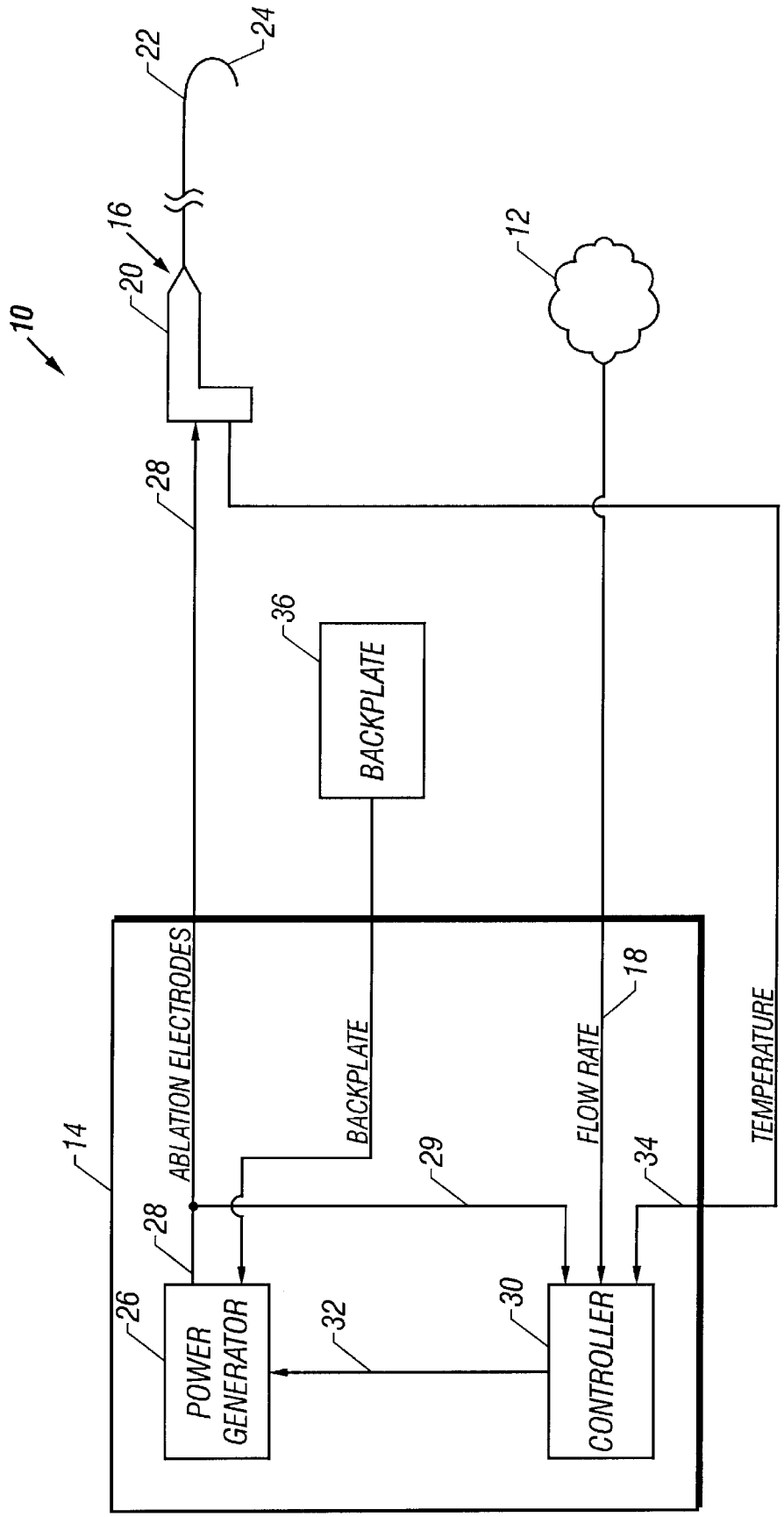
FIG. 1 is a schematic block diagram of an ablation system configured in accordance with aspects of the invention including a power control system ("PCS"), a catheter system and a means for obtaining fluid-flow rate information from a biological site.

Turning now to the drawings, in which like reference numerals are used to designate like or corresponding elements among the several figures, in FIG. 1 there is shown a system 10 for use in ablation therapy of a biological site 12, e.g., the atrium or ventricle of the heart. The system 10 includes a power control system 14, a catheter system 16, and means (not shown) for providing flow rate information 18 to the power control system 14. The flow rate information 18 includes data indicative of the rate of fluid flow through the biological site 12, such as blood through the heart. The catheter system 16 includes a handle 20 and a steerable catheter sheath 22 having a distal segment 24. The distal segment 24 carries an electrode system (not shown) and is capable of being percutaneously introduced into a biological site.

As described in detail below, in one embodiment of the invention, the flow rate information is provided by one or more ECG sensors that sense the electrical activity of the biological site. In another embodiment of the invention, the flow rate information is provided by one or more flow sensors positioned within the biological site. With regard to the ECG embodiment of the invention, the ECG sensors may be either external or internal sensors. An external ECG sensor may include a plurality of individual sensors placed on the various locations on the surface of the biological site, e.g., patient's skin. An internal ECG sensor may include sensors adapted to be positioned within the biological site. In one configuration of the ECG embodiment of the invention, described in detail below, the internal ECG sensors comprise electrodes carried by the catheter system 16. In either case, the signals sensed by the ECG sensors are processed by a standard ECG signal analyzer. The ECG signal analyzer may be a stand alone device adapted to forward analysis results to the power control system 14.

Alternatively, the ECG signal analyzer may be incorporated into the power control system 14. The ECG sensors in combination with the standard ECG signal analyzer define an "ECG device." The power control system 12 includes a power generator 26, that may have any number of output channels through which it provides power or drive 28 to the catheter system 16. The operation of the power generator 26 is controlled by a controller 30 which outputs control signals 32 to the power generator 26. The controller 30 monitors the power 28 provided by the power generator 26 along a power monitor line 29. In addition, the controller 30 also receives temperature signals 34 from the catheter system 16 and receives and flow rate information 18 from either the catheter system or from other sources. Based on the power 28, the temperature signals 34 and the flow rate data 18 the controller 30 adjusts the operation of the power generator 26.

The system 10 may further include a backplate 36. The backplate 36 is connected to the power generator 26 and generally provides a return path for the power 28 delivered to the biological site 12 through the catheter system 16.

Figures 1, 5:
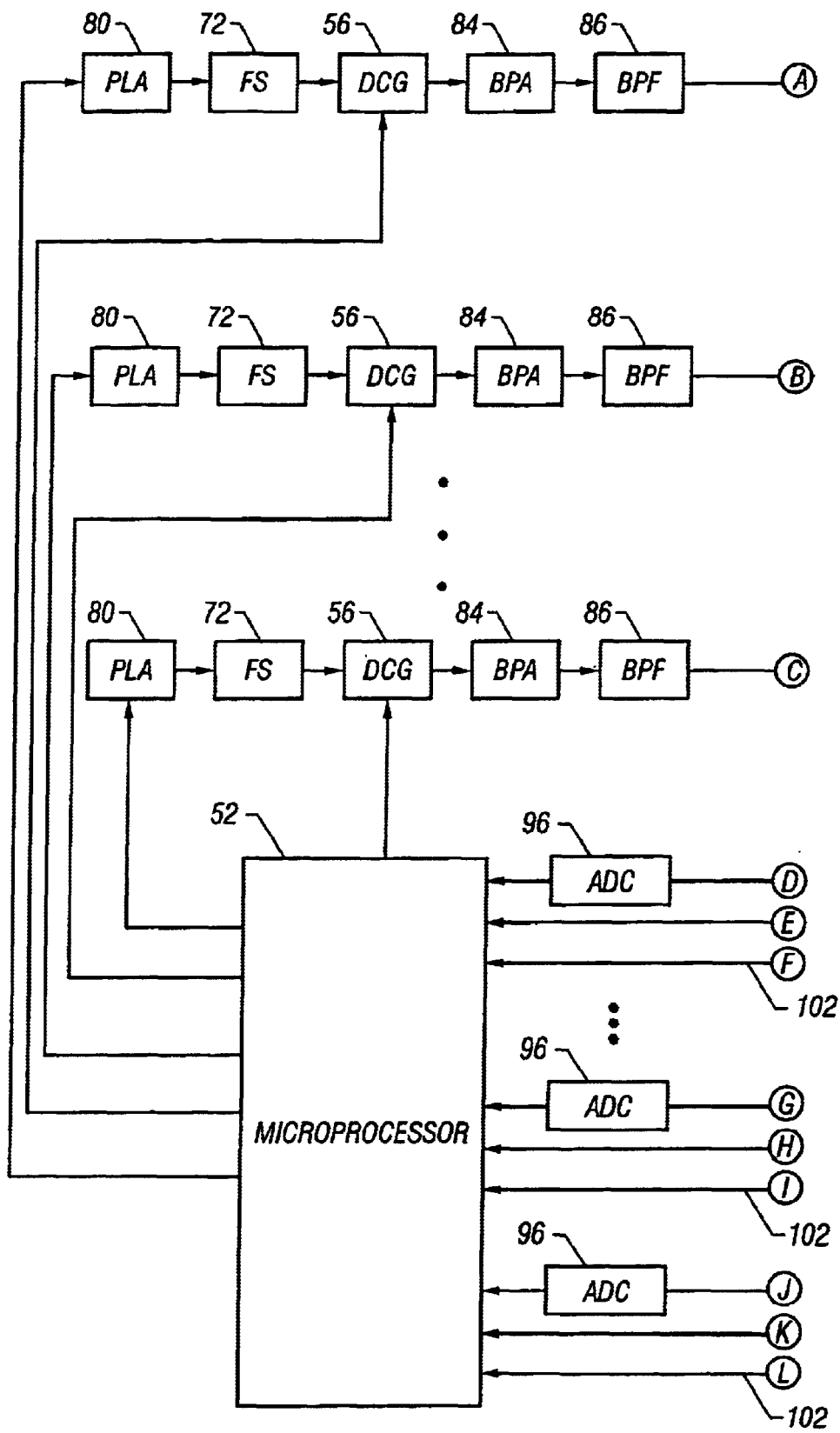
Figures 2, 5:
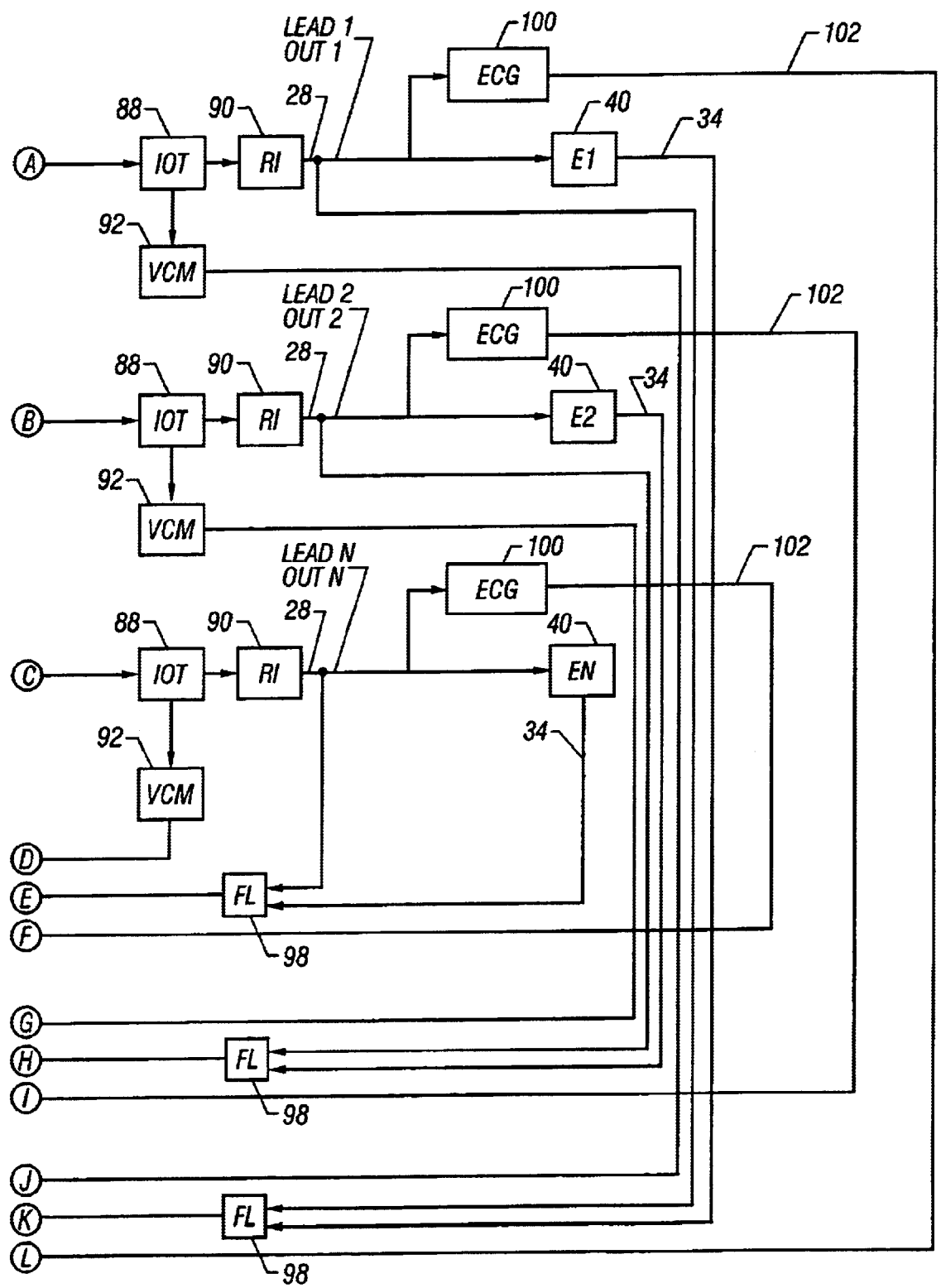

As shown in FIGS. 2 and 3, the distal segment 24 of the catheter system 16 includes an electrode system 38 (FIG. 3). The electrode system 38 is shown in schematic form with the components drawn in more detail to more clearly illustrate the relationship between the components. A preferred embodiment of the electrode system 38 includes twelve band electrodes 40 arranged in a substantially linear array along the distal segment 24 of the catheter sheath 22. The electrode system 38 may include a tip electrode 42. (For clarity of illustration, only four band electrodes 40 are shown in FIG. 3 although as stated, a preferred embodiment may include many more.) The band electrodes 40 are arranged so that there is space 44 between adjacent electrodes. In one configuration of the electrode system 38, the width of the band electrodes 40 is 3 mm and the space 44 between the electrodes is 4 mm. The total length of the electrode system 38, as such, is approximately 8 cm.

The arrangement of the band electrodes 40 is not limited to a linear array and may take the form of other patterns. A substantially linear array is preferred for certain therapeutic procedures, such as treatment of atrial fibrillation, in which linear lesions of typically 4 to 8 cm in length are desired. A linear array is more easily carried by the catheter sheath 22 and also lessens the size of the catheter.

The band electrodes 40 are formed of a material having a significantly higher thermal conductivity than that of the biological tissue to be ablated. Possible materials include silver, gold, chromium, aluminum, molybdenum, tungsten, nickel, platinum, and platinum/10% iridium. Because of the difference in thermal conductivity between the band electrodes 40 and the tissue, the electrodes cool off more rapidly in the flowing fluids at the biological site. The band electrodes 40 are sized so that the surface area available for contact with fluid in the heart, e.g., blood, is sufficient to allow for efficient heat dissipation from the electrodes to the surrounding blood. In a preferred embodiment, the electrodes 40 are 7 French (2.3 mm in diameter) with a length of 3 mm.

Associated with the electrode system 38 are thermal sensors 46 for monitoring the temperature of the electrode system 38 at various points along its length. In one embodiment, each band electrode 40 has a thermal sensor 46 mounted to it. Each thermal sensor 46 provides a temperature signal 34 (FIG. 1) to the controller 30 which is indicative of the temperature of the respective band electrode 40 (FIGS. 2 and 3) at that sensor. In another embodiment of the electrode system 38 a thermal sensor 46 is mounted on every other band electrode 40. Thus for a catheter having twelve electrodes, there are thermal sensors on six electrodes. In yet another embodiment of the electrode system 38 every other electrode has two thermal sensors 46. In FIG. 3, which shows an embodiment having one thermal sensor for each electrode, there is shown a single power lead 48 for each electrode 40 to provide power to each electrode for ablation purposes and two temperature leads 50 for each thermal sensor 46 to establish a thermocouple effect.

Figure 4A:
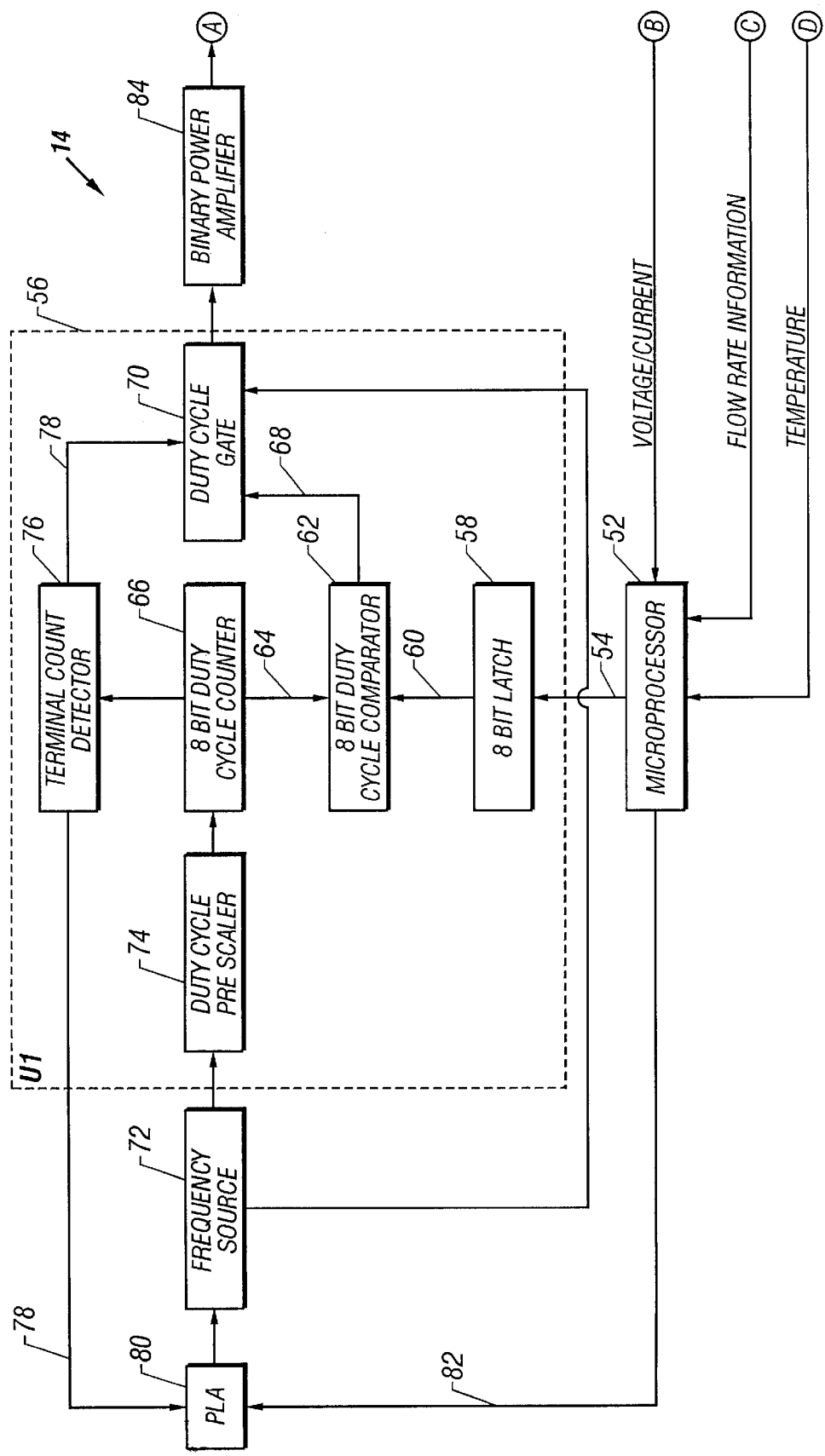
FIGS. 4A and 4B form a block diagram presenting a detailed configuration of one embodiment of the ablation system of FIG. 1 wherein the fluid-flow rate information is obtained using an electrocardiogram (ECG) device.
Figure 4B:
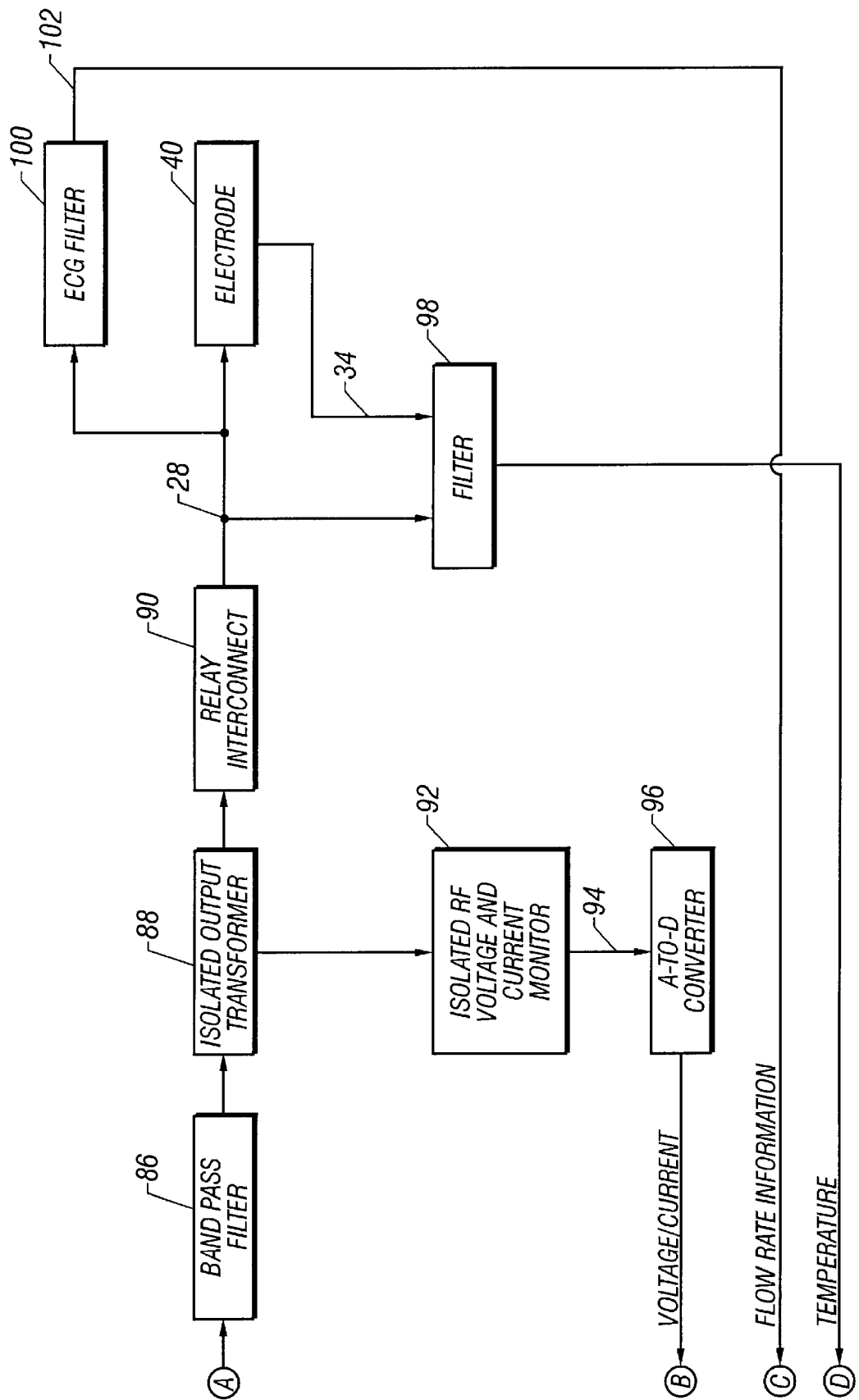

Turning now to FIGS. 4A and 4B, one configuration of an ablation system employs an internal ECG sensor, i.e., band electrode 40, and a single channel power control system 14 for use with a catheter system carrying the single band electrode. The system includes an ECG filter 100 for filtering the signals sensed by the electrode 40 and an ECG signal analyzer that is programmed into a power control system ("PCS") microprocessor 52. As will be discussed in relation to other figures, an ablation system may include a multichannel power control system 14 for use with a catheter system having a plurality of ECG sensors, i.e., band electrodes 40, and ECG filters 100.

In FIG. 4A, the PCS microprocessor 52, which is part of the controller 30 (FIG. 1), provides a duty cycle control signal 54 to a duty cycle generator ("DCG") 56. In this case, the duty cycle generator 56 receives the control signal 54 by an 8-bit latch 58. The latch 58 provides an 8-bit signal 60 to a duty cycle comparator 62. The comparator 62 compares the 8-bit signal 60 to a count 64 from an 8-bit duty cycle counter 66 and if the count is the same, provides a duty cycle off signal 68 to the duty cycle gate 70. The gate 70 is connected to a frequency source ("FS") 72, such as an oscillator that produces a 500 kHz signal. When the gate 70 receives the duty cycle off signal 68 from the comparator 62, it stops its output of the frequency source signal through the gate and no output exists.

At a frequency of 500 kHz, an 8-bit control has a period or time frame of 0.5 msec. At a fifty-percent duty cycle, the electrode is in the off period only 0.25 msec. The period or time frame is lengthened by use of a prescalar 74 interposed between the frequency source 72 and the counter 66. In one embodiment, the prescalar 72 lengthens the period to 4 msec thus allowing for a 2 msec off period during a fifty-percent duty cycle. Other lengths of the period may be used depending on the circumstances. It has been found that a ten percent duty cycle is particularly effective in ablating heart tissue.

A terminal count detector 76 detects the last count of the period and sends a terminal count signal 78 to the gate 70 which resets the gate for continued output of the frequency source signal. This then begins the on period of the duty cycle and the counter 66 begins its count again. In one preferred embodiment, the duty cycle is set at fifty percent and the 8-bit latch is accordingly set to 128. In another embodiment, the duty cycle is set at ten percent.

A programmable logic array ("PLA") 80 receives phase control signals 82 from the PCS microprocessor 52 and controls the phase of the frequency source 72 accordingly. In one embodiment, the PLA 80 receives the terminal count signal 78 from the terminal count detector 76 and only permits phase changes after receiving that terminal count signal.

The output signal from the gate 70 during the on-period of the duty cycle is provided to a binary power amplifier ("BPA") 84 that increases the signal to a higher level, in this case, 24 volts. The amplified signals are then filtered with a band pass filter ("BPF") 86 to convert the somewhat square wave to a sine wave. The band pass filter 92 in one embodiment is centered at 500 kHz. The filtered signal is then provided to an isolated output transformer ("IOT") 88 that amplifies the signal to a much higher level, for example 350 volts peak-to-peak. This signal is then sent to a relay interconnect ("RI") 90 before it is provided as a power output signal OUTn 28 to the electrode 40.

In the embodiment shown in FIGS. 4A and 4B, a voltage and current monitor ("VCM") 92 is used. The monitor signal 94 is converted to digital form by an A-to-D converter ("ADC") 96 and provided to the PCS microprocessor 52. As previously mentioned, some or all of the electrodes 40 may include a thermal sensor 46 (FIG. 3) that provides temperature signals 34 (FIG. 4B) which are used to determine the temperature at the electrode 40. In one embodiment of the invention, the power 28, in conjunction with the temperature signals 34, are used to determine the temperature at the electrode 40. Both the temperature signals 34 and the power 28 pass through a temperature filter ("FL") 98 before being sent to the PCS microprocessor 52. In the alternative, the temperature filter 98 is contained in a printed circuit board separate from the controller 30 and contains its own processor. In either case, the filter 98 filters out any RF noise present in the power 28 so that the signal may be used for temperature monitoring purposes.

At the ECG filter 100 the power signal 28 is filtered to remove the 500 kHz frequency component, thus providing an ECG signal 102 that is free of high frequency interference. The ECG signal 102 thus comprises low frequency electrical signals, typically between 0 and 250 Hz, detected in the biological tissue by the ablation electrode 40. The ECG signal 102 is then sent to the PCS microprocessor 52 where it is processed along with the temperature signals 34 to control the application of RF energy. As explained below, the ECG filter 100 allows for continuous ECG analysis of the tissue to occur simultaneously with the application of ablation energy.

Referring now to FIGS. 5-1 and 5-2, a block diagram of a multi-channel ablation system with a plurality of ECG filters 100 for use with a catheter system having a plurality of ablation electrodes 40, i.e., internal ECG sensors, is shown. Although only three complete channels are shown, the system comprises many more as indicated by the successive dots. Those channels are not shown in FIGS. 5-1 and 5-2 to preserve clarity of illustration.

The single PCS microprocessor 52, which again is part of the controller 30 (FIG. 1), controls the duty cycle and the phase of each channel individually in this embodiment. Each channel shown comprises the same elements and each channel produces its own power output signal 28 (OUT1, OUT2, through OUTn where "n" is the total number of channels) on respective electrode leads (LEAD 1, LEAD 2, through LEAD n where "n" is the total number of leads) to its respective electrode 40.

Figure 6C:
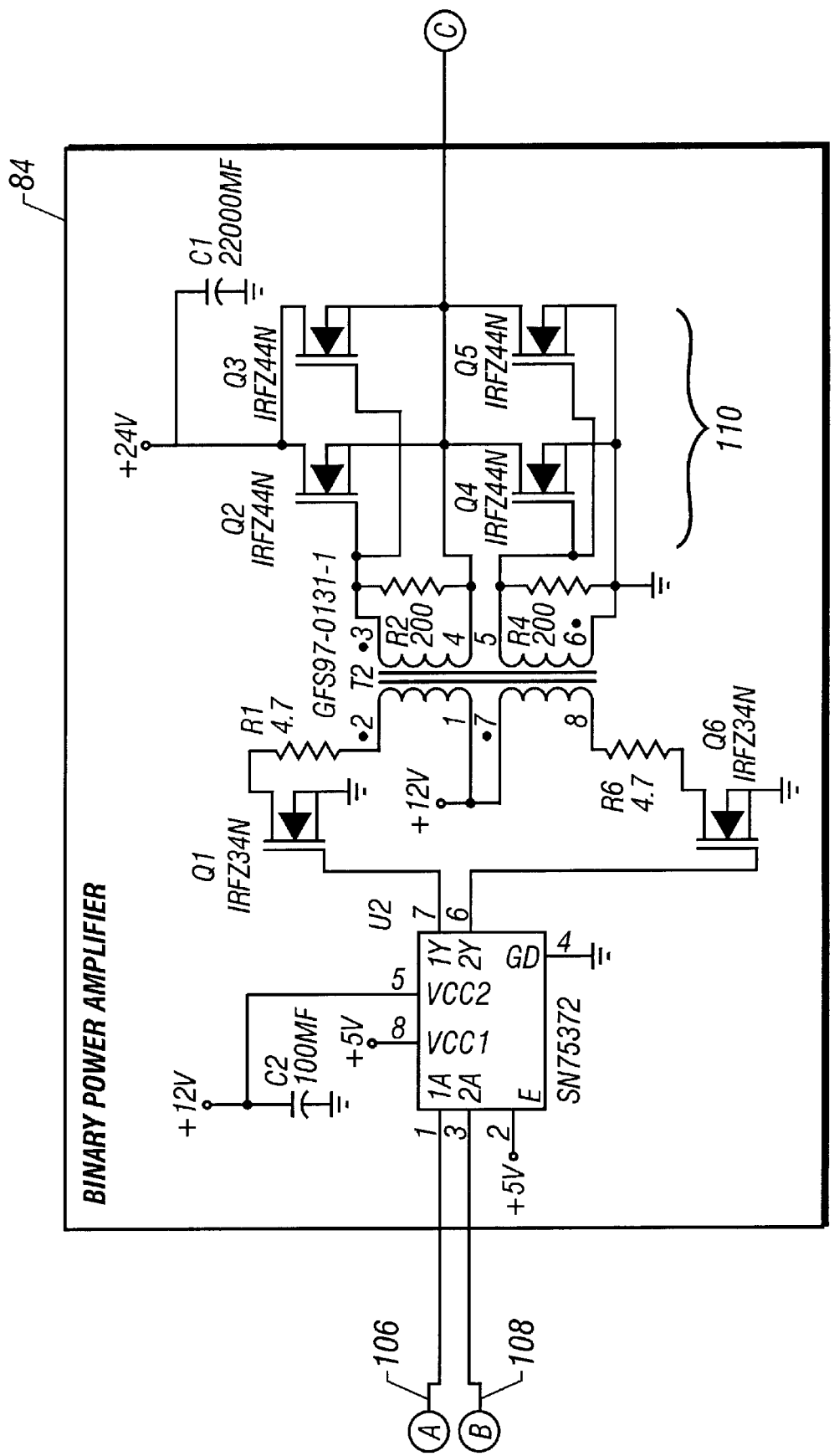
Figure 6D:
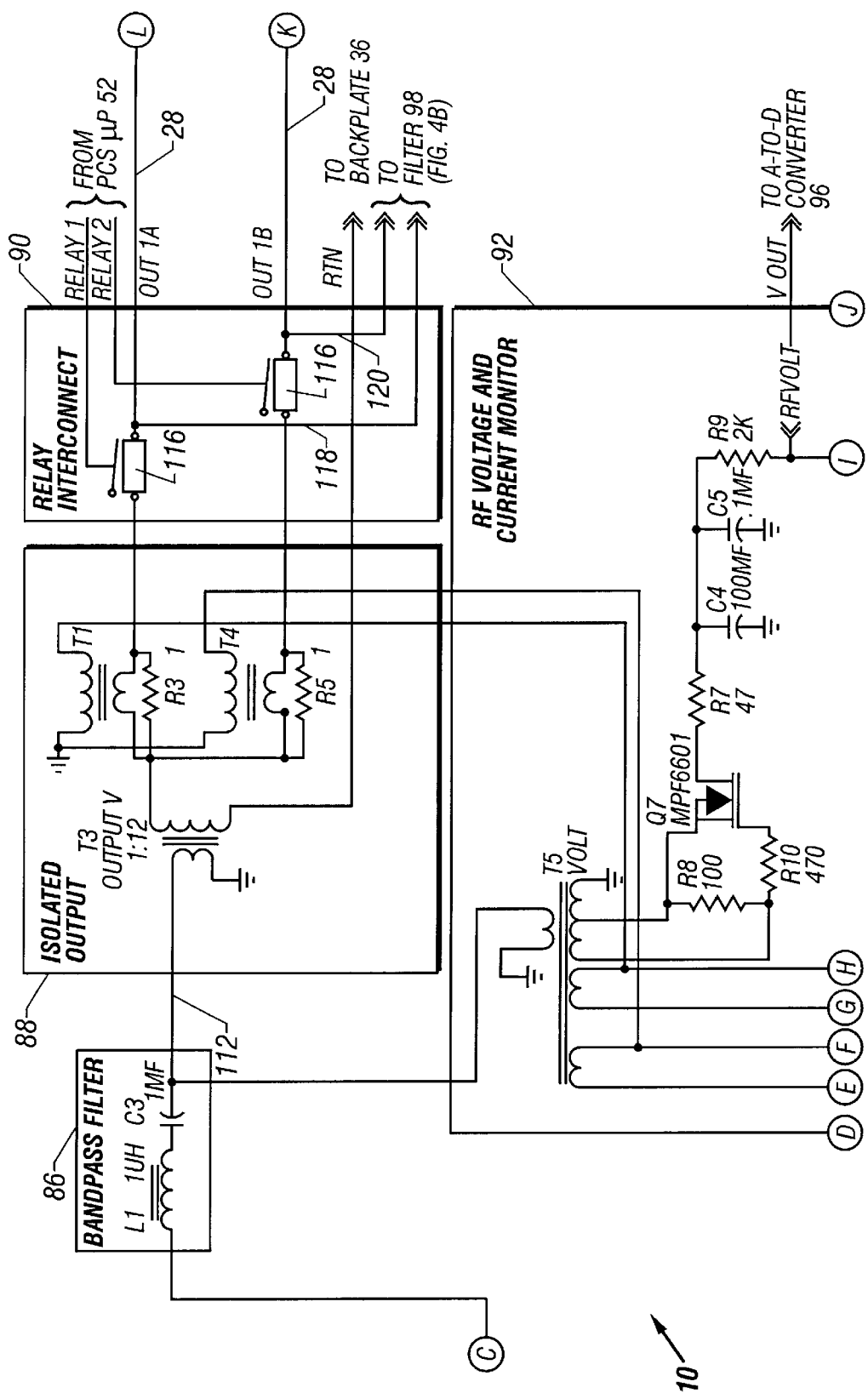
Figure 6E:
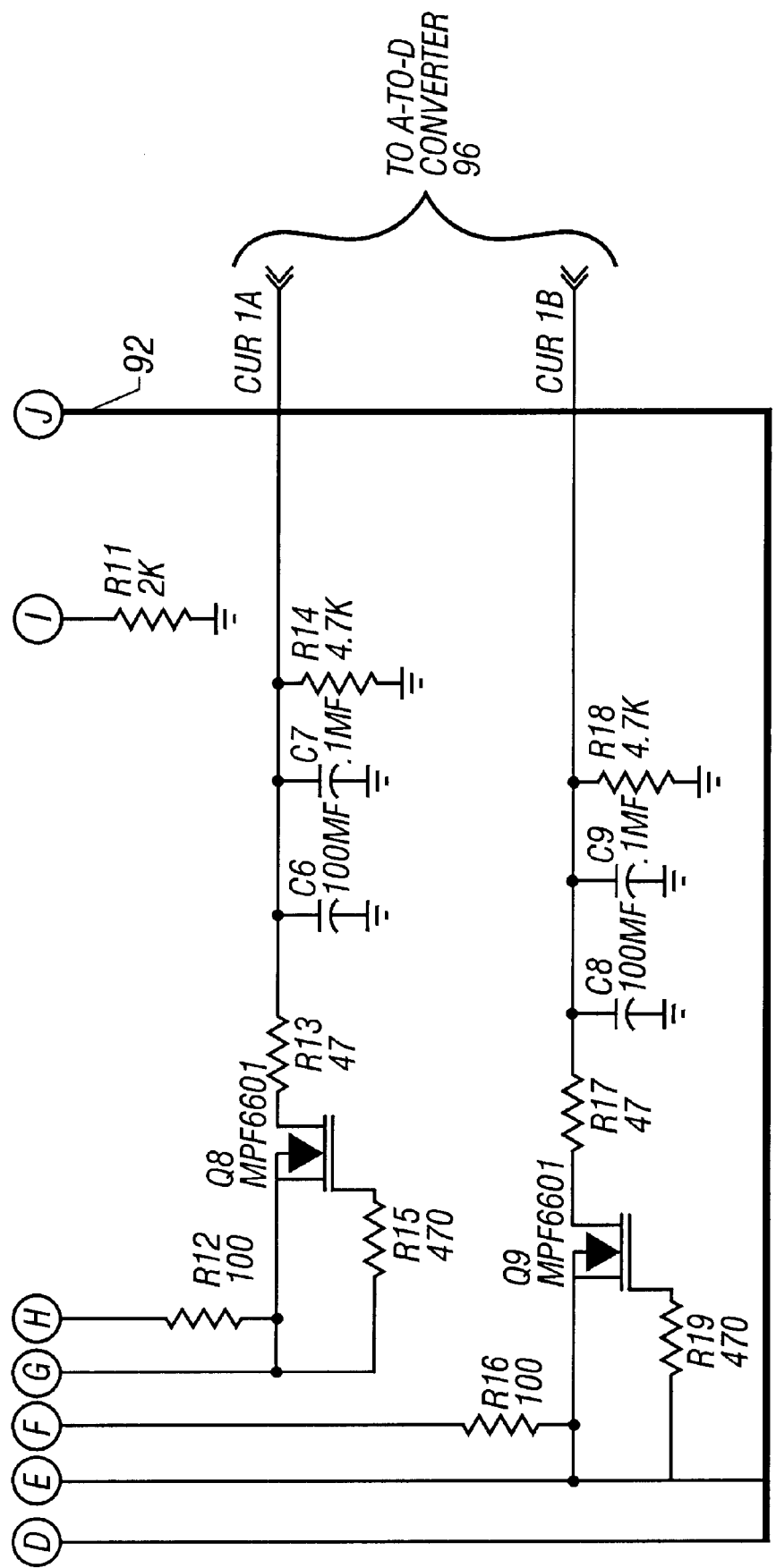
Figure 6F:
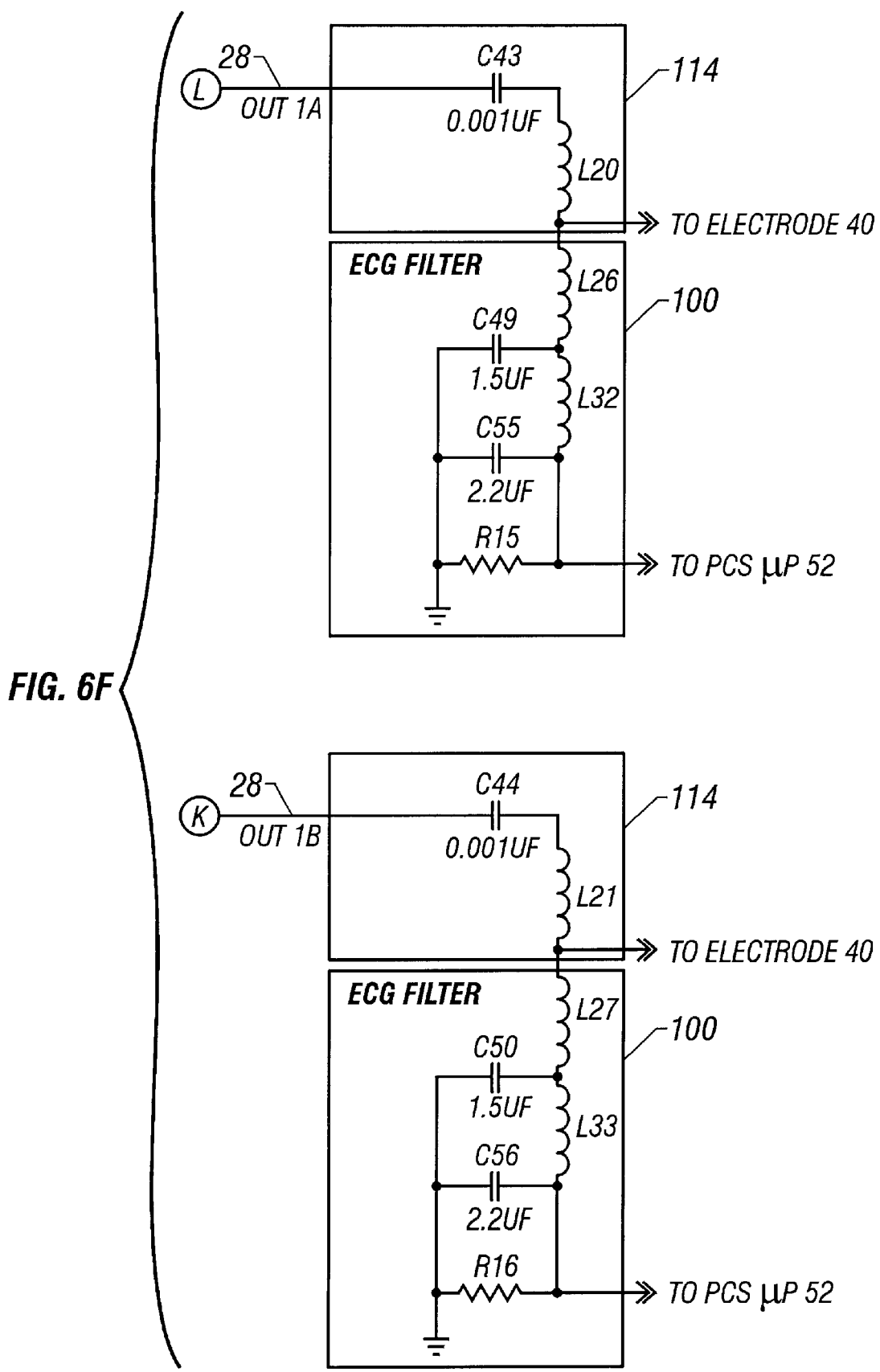

With reference now to FIGS. 6A through 6F, a schematic diagram of an embodiment of the power control system 14 is presented in FIGS. 6B through 6F while FIG. 6A shows how FIGS. 6B through 6F should be oriented in relation to each other. The frequency source 72 provides a signal 104, typically at 500 kHz with a phase angle controlled by the PCS microprocessor 52 through the PLA 80, to the duty cycle generator 56. The duty cycle generator 56 modulates the frequency source signal 104 to produce the selected duty cycle in accordance with the duty cycle control signal as previously described. The duty cycle generator 56 outputs two signals 106 and 108 to the binary power amplifier 84. A dual MOSFET driver U2 receives the signals, converts their 5V level to a 12V level, and sends each to a transformer T2 which transforms the signals into 24 V peak-to-peak power.

The 24V power is then sent to a multi-state driver 110 which includes a configuration of FETs Q2, Q3, Q4, and Q5. During a conducting state of the driver 110, which is typically the on period of the power, these FETs Q2 through Q5 conduct and forward the power to a bandpass filter 86 comprising a series LC network. During a high-impedance state of the driver 110, which is typically during the off period of the power, the FETs Q2 through Q5 are nonconducting and no power is sent to the bandpass filter 86. Instead the FETs Q2 through Q5 present a high impedance load to any signals received through the electrode 40. Typically the load impedance on the FETs Q2 through Q5 presented by the circuit following the FETs, the electrode, and the tissue is approximately 150 $\Omega$ but transformed through the output transformer T3, it presents a load impedance to the FETs Q2–Q5 of approximately 0.5 to 1 $\Omega$. In the off state, the FETs present an impedance of approximately 250 $\Omega$ which is large in comparison to the transformed load impedance of approximately 0.5 to 1 $\Omega$. Therefore, very little power flows when the FETs are in the off state.

The bandpass filter 86 operates to shape the output signal provided by the binary amplifier 84 from a square wave to a sinusoidal wave. The filtered signal 112 then passes to the isolated output section 88 where it is step-up transformed to 350 volt peak-to-peak sinusoidal power at T3. The power is then split into two identical power signals OUT1A, OUT1B. Each of OUT1A and OUT1B is provided to an LC series resonant circuit 114 which ensures that the signal is at or near the ablation frequency, e.g., approximately 500 kHz. Each of OUT1A and OUT1B is then provided to two or more respective band electrodes 40 on the output lines LEAD1A, LEAD1B.

During ECG analysis, ECG signals from the band electrodes 40 are fed from the electrode to an ECG filter 100 comprising a $4^{th}$ order Butterworth filter. The ECG signals are fed over the same output line that carries OUT1A and OUT1B to the electrode 40. These ECG signals comprise generally low-frequency signals present in the biological tissue. Also input to the ECG filter 100 is the output of the LC series resonant circuit 114, which is essentially the high-frequency ablation signal, which is typically around 500 kHz. The ECG filter 100 filters out the high-frequency ablation signal, leaving only lower frequency components. This lower frequency, ECG signal is then fed to the PCS microprocessor 52 for ECG signal analysis.

The relay interconnect 90 includes relays 116 that may be individually opened to remove the power signals OUT1A, OUT1B from the electrode leads LEAD 1A, LEAD 1B when an alert condition is detected, such as high temperature at the respective electrode 40. As previously mentioned these conditions are determined by the PCS microprocessor 52 which receives signals indicative of the temperature and fluid-flow rate at each of the electrodes 40.

The power from the isolated output section 88 is monitored and representative signals are supplied to a RF voltage and current monitor 92 where in this case, the voltage and current of each output signal are measured to determine the impedance of the particular channel. The measured signals are sent to an A-to-D converter 96 before being sent to the PCS microprocessor 52 for impedance monitoring. If the impedance is above a threshold level indicative of blood clotting or boiling, the PCS microprocessor 52 sends a signal to the duty cycle generator 56 to reduce or discontinue the duty cycle of the power OUT1A, OUT1B and thus lower the effective power delivered to the electrodes 40.

Similarly, the temperature at the electrodes 40 is determined by monitoring the power and temperature signals and measuring the voltage difference between the signals. As previously mentioned, in one embodiment of the invention, these signals pass through a filter 98 (FIG. 4B) before being sent to the PCS microprocessor 52. The voltage value is converted to a temperature and if the temperature is above a threshold level the duty cycle of the power 28 is reduced. In the case where a single lead is used to provide a signal which is used to determine the temperature as well as provide power to the electrode 40, the signal from the lead is received on temperature leads 118, 120 connected at the output side of the relays 116. An example of a single-lead configuration is described in U.S. Pat. No. 6,049,737, the disclosure of which is hereby incorporated by reference.

The rate of fluid flow through the biological site is determined by monitoring the ECG signals. As described in detail below, the PCS microprocessor adjusts the level of RF energy applied to the electrodes based on the flow rate and the temperature of the electrode.

Referring to FIGS. 6B through and 6E, the following devices are shown:

| Device | Part No. | Manufacturer |
| --- | --- | --- |
| U1 | GAL6002B | Lattice |
| U2 | SN75372 | numerous |
| Q1 | 1RFZ34N | numerous |
| Q2, Q3, Q4, Q5 | 1RFZ44N | numerous |
| Q7, Q8, Q9 | MPF6601 | numerous |
| R3, R5 | 1Ω | numerous |
| T1, T4 | CMI-4810 | Corona Magnetics, Inc. |
| T2 | GFS97-0131-1 | GFS Manufacturing |
| T5 | CMI-4809 | Corona Magnetics, Inc. |

The transformer denoted by "T3" is a 1:12 turns ratio, single turn primary, step up transformer wound on a TDK core PC50EER23Z.

The ECG embodiment of the system thus described has two primary modes of operation: a constant power mode and an automatic temperature control mode. Once the catheter system is properly positioned within the biological site, e.g., the heart, operation of the system may proceed under either mode.

Figure 7:
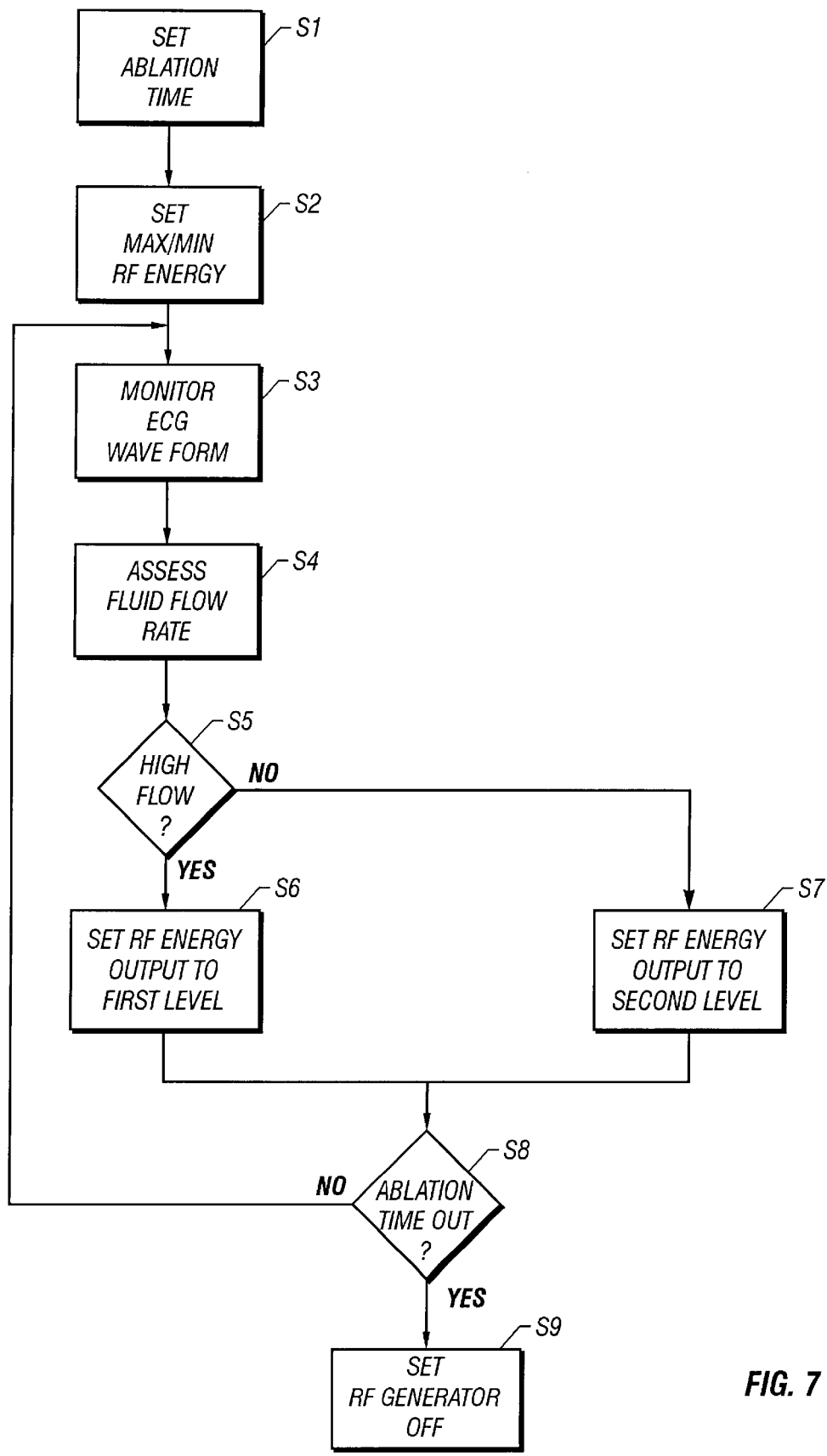
FIG. 7 is a flow chart of the operation of the ECG system of FIGS. 4A and 4B when in a constant power mode.

With reference to FIG. 7, when operating in a constant power mode, at step S1, the user sets an ablation time and, at step S2, a maximum RF energy level value and a minimum RF energy level value which is less than the maximum value. These values are selected by the user based on various factors, including the biological site being ablated, the location of the ablation area within the biological site, the thermal, electrical and optical properties of the tissue being ablated, the degree of contact between the electrode and the tissue and the desired characteristics of the ablation lesion desired, i.e., size and depth of lesion. The energy level and time values may be set through front panel controls on the RF generator.

At step S3, ECG signals are collected by the ECG sensors, i.e., band electrodes, associated with the catheter and are sent to the PCS microprocessor, where the ECG waveforms defined by the ECG signals are monitored. At step S4, the flow rate of fluid through the biological site, e.g., blood through the heart, is assessed by the PCS microprocessor. The PCS microprocessor is programmed to perform standard ECG signal analysis functions and to accordingly, recognize various ECG waveforms. Implementation of these functions is based on common recognition pattern algorithms well known in the art of ECG analysis. As such a detailed description of these algorithms is not presented. As described further below, The PCS microprocessor is further programmed to identify "high" and "low" flow rates based on the recognized waveforms.

At steps S5 the PCS microprocessor determines whether the flow rate is high or low. If the flow rate is high, at step S6 the PCS microprocessor controls the output of RF energy from the RF generator such that RF energy of a first level is applied to the electrode. This first level of energy is substantially equal to the maximum RF energy level selected by the user. If the flow rate is low, at step S7 the PCS microprocessor controls the output of RF energy from the RF generator such that RF energy of a second level is applied to the electrode. This second level of energy is substantially equal to the minimum RF energy level selected by the user and is usually at or near zero.

In the configuration of the RF generator described herein, the level of RF energy output is adjusted by controlling the duty cycle of the power. Increasing the duty cycle effects a corresponding increase in the energy output. Likewise, decreasing the duty cycle decreases the energy output. In alternate configurations of the RF generator, adjustments to energy outputs may be made by adjusting the amplitude of the power.

At step S8, the PCS microprocessor determines whether the ablation time has expired. If the time has not expired, the operation process returns to step S3 and continues to monitor the ECG waveform. If the ablation time has expired, the PCS microprocessor sets the RF generator off at step S9.

Figure 8:
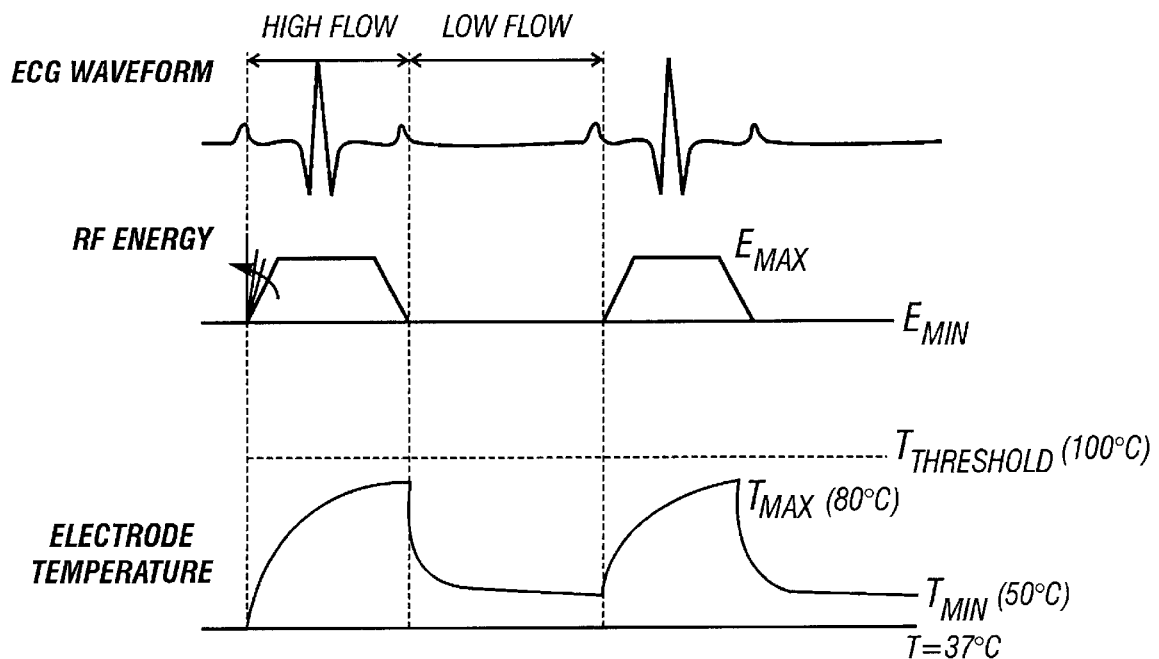
FIG. 8 is a graph depicting ECG waveforms during normal sinus rhythm (NSR), corresponding constant power RF energy applied during NSR and resultant electrode temperature, each depicted as a function of time.

As previously mentioned, the PCS microprocessor is programmed to recognize various ECG waveforms and to identify "high" and "low" flow rates accordingly. One such ECG waveform recognized by the PCS microprocessor is shown in FIG. 8. This waveform is known as a PQRST waveform and depicts electromotive force changes in the human body, which rise and fall with each heart beat to produce a sequence of alternating P, Q, R, S, and T waveforms. A RF-energy-level-verses-time graph, as provided by the system, is shown beneath the ECG waveform with the resulting electrode-temperature-verses-time curve shown below the RF energy graph.

As previously mentioned, the PCS microprocessor is adapted to assess the fluid-flow rate in the biological organ. The PCS microprocessor is programmed to identify high biological fluid-flow periods as those periods occurring between a P wave of the PQRST waveform and its subsequent T wave and low biological fluid-flow periods as those periods in the PQRST waveform occurring between a T wave and the next P wave.

As shown in FIG. 8, at the beginning of a high flow rate period, as indicated by a P wave, the RF energy level is ramped up from the first, minimum value, e.g., zero, to the second, maximum value which is greater than the first value. The RF energy is applied at a constant level during most of the PQRST waveform. The PCS microprocessor, programmed to function as a common ECG signal analyzer, detects the beginning and end of an "S" wave and uses the end of the "S" wave as a signal to begin ramping down the RF energy. The energy is ramped down at a rate such that at the end of the T wave the energy level is at or near the first, minimum value. The energy remains at this level throughout the low flow rate period, until the next P wave, at which time the RF energy is again ramped up to the second value.

As indicated by the electrode-temperature-verses-time curve, during high flow rate periods, when maximum RF energy is applied to the electrode, the temperature of the electrode approaches a target maximum temperature. As previously mentioned, the system provides temperature feedback signals to the PCS microprocessor. The PCS microprocessor monitors the temperature of the electrode and is adapted to ensure that the RF energy provided by the RF generator allows the electrode temperature to approach the target maximum temperature without exceeding a threshold maximum temperature. The target temperature and threshold temperature may be programmed into the PCS microprocessor through front panel controls. For ablation procedures performed in the heart, the target maximum temperature is preferably between approximately 50° C. and approximately 80° C. Because blood coagulation is known to occur at 100° C. the threshold maximum temperature is approximately 100° C. If the threshold maximum temperature is exceeded, the PCS microprocessor shuts down the RF generator.

With continued reference to the electrode-temperature-verses-time curve of FIG. 8, during low flow rate periods, the minimum RF energy is applied to the electrode. As previously mentioned, minimum RF energy is less than the maximum RF energy and is generally at or near zero. With the RF energy at a substantially reduced level, the temperature of the electrode is able to approach a target minimum temperature, which is preferably 50° C. Again, the target minimum temperature may be entered into the PCS microprocessor.

Figure 9:
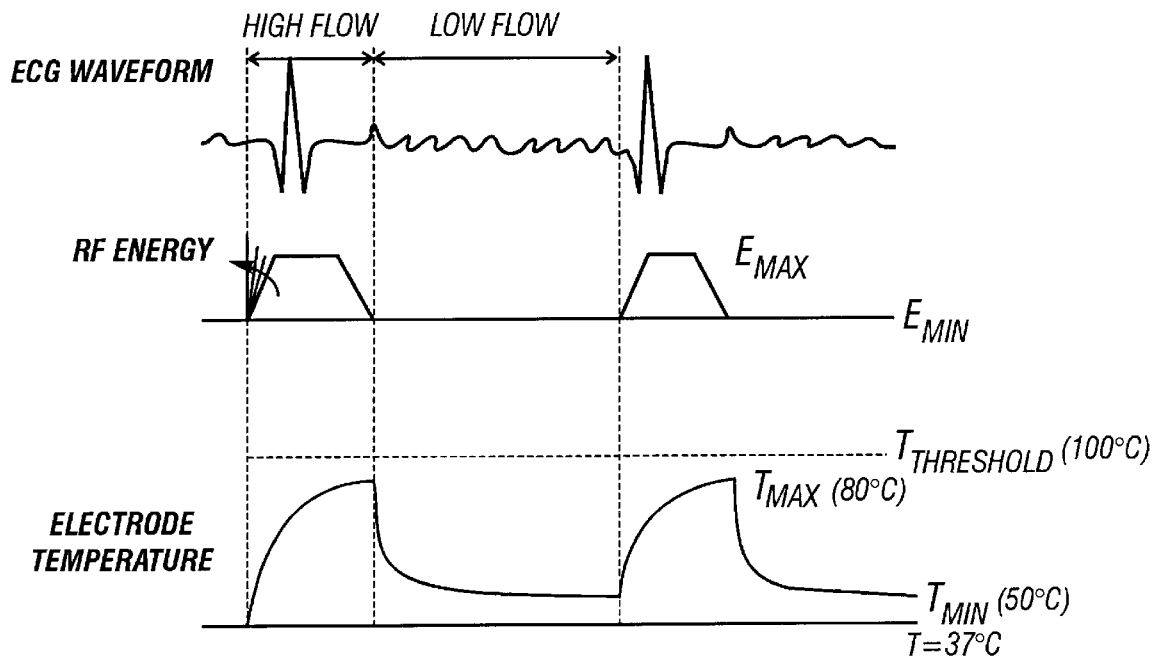
FIG. 9 is a graph depicting ECG waveforms during atrial fibrillation (AF), corresponding constant power RF energy applied during AF and resultant electrode temperature, each depicted as a function of time.

Another ECG waveform, i.e., the QRS complex waveform, recognized by the PCS microprocessor is shown in FIG. 9. The QRS complex waveform is indicative of irregular heart movements associated with atrial fibrillation. A RF-energy-level-verses-time graph, as provided by the system, is shown beneath the ECG waveform with the resulting electrode-temperature-verses-time curve shown below the RF energy graph.

The PCS microprocessor is programmed to identify high biological fluid-flow periods as those periods occurring between a QRS wave and its subsequent T wave. Periods of low fluid-flow are identified as those periods occurring between a T wave and the next QRS wave. During periods of high fluid-flow, the RF generator increases the energy to achieve the selected maximum RF energy level and applies energy at a constant level. During periods of low fluid-flow the RF generator reduces the energy level to the minimum RF energy level selected by the user, which usually is at or near zero.

As shown in FIG. 9, at the beginning of a high flow rate period, as indicated by the onset of a QRS wave, the RF energy level is ramped up from the first, minimum value, e.g., zero, to the second, maximum value which is greater than the first value. The RF energy is applied at a constant level until a time just prior to the T wave when the RF energy is ramped down. The energy is ramped down at a rate such that at the end of the T wave the energy level is at or near the first, minimum value. The energy remains at this level throughout the low flow rate period, until the onset of the next QRS wave, at which time the RF energy is again ramped up to the second value.

As indicated by the electrode-temperature-verses-time curve, during high flow rate periods, when maximum RF energy is applied to the electrode, the temperature of the electrode approaches a target maximum temperature and during low flow rate periods, when minimum RF energy is applied to the electrode, the temperature of the electrode approaches a target minimum temperature. As a safeguard against exceeding a threshold maximum temperature for a period of time, the PCS microprocessor shuts down the RF generator whenever the threshold maximum temperature is exceeded.

Figure 10:
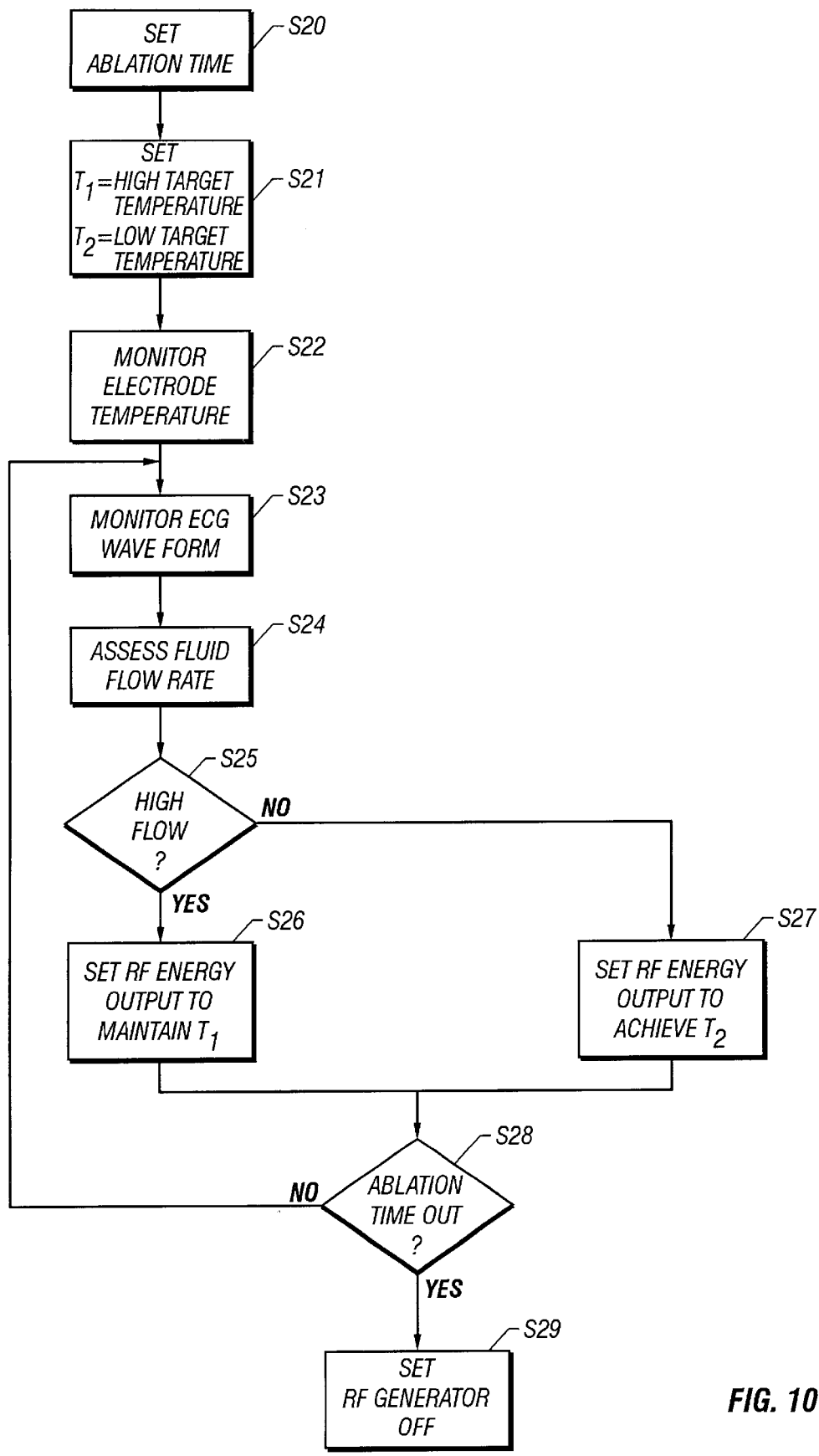
FIG. 10 is a flow chart of the operation of the ECG system of FIGS. 4A and 4B when in the automatic temperature controlled mode.

With reference to FIG. 10, when operating in the automatic temperature control mode, at step S20, the user sets an ablation time and, at step S21, a high target temperature and a low target temperature. These values are selected by the user based on various factors, including the biological site being ablated, the location of the ablation area within the biological site, the thermal, electrical and optical properties of the tissue being ablated, the degree of contact between the electrode and the tissue and the desired characteristics of the ablation lesion desired, i.e., size and depth of lesion. A typical high target temperature used for ablation procedures in the heart is between approximately 50° C. and approximately 80° C., while a typical low target temperature is between approximately 42° C. and approximately 50° C. The temperature and time values may be set through front panel controls of the RF generator.

At step S22, the PCS microprocessor monitors the electrode temperature using the temperature feedback signals provided by the thermal sensor on the electrode. At step S23, ECG signals are collected by the ECG sensors associated with the catheter and are sent to the PCS microprocessor, where the ECG waveforms defined by the ECG signals are monitored. At step S24, the flow rate of fluid through the biological site, e.g., blood flow through the heart, is assessed by the PCS microprocessor. As described above, the PCS microprocessor is programmed to recognized PQRST (FIG. 11) and QRS complex (FIG. 12) ECG waveforms and to identify "high" and "low" flow rates accordingly.

At step S25 the PCS microprocessor determines whether the flow rate is high or low. If the flow rate is high, at step S25 the PCS microprocessor controls the output of RF energy from the RF generator such that the RF energy provided to the electrode allows the electrode temperature to approach the high target temperature without exceeding a threshold maximum value which is approximately 100° C. If the threshold maximum temperature is exceeded, the PCS microprocessor shuts down the RF generator. If the PCS microprocessor determines that the fluid-flow rate is low, at step S27 the PCS microprocessor controls the output of RF energy from the RF generator such that the RF energy provided to the electrode allows the electrode temperature to approach the low target temperature.

At step S28, the PCS microprocessor determines whether the ablation time has expired. If the time has not expired, the operation process returns to step S23 and continues to monitor the ECG waveform. If the ablation time has been exceeded, the PCS microprocessor sets the RF generator off at step S29.

As previously mentioned, the PCS microprocessor is programmed to recognize the same ECG waveforms and to identify "high" and "low" flow rates accordingly, as previously discussed with regard to the constant power mode. These ECG waveforms are shown in FIGS. 11 and 12, along with their corresponding RF-energy-level-verses-time graphs and electrode-temperature-verses-time curves.

Figure 11:
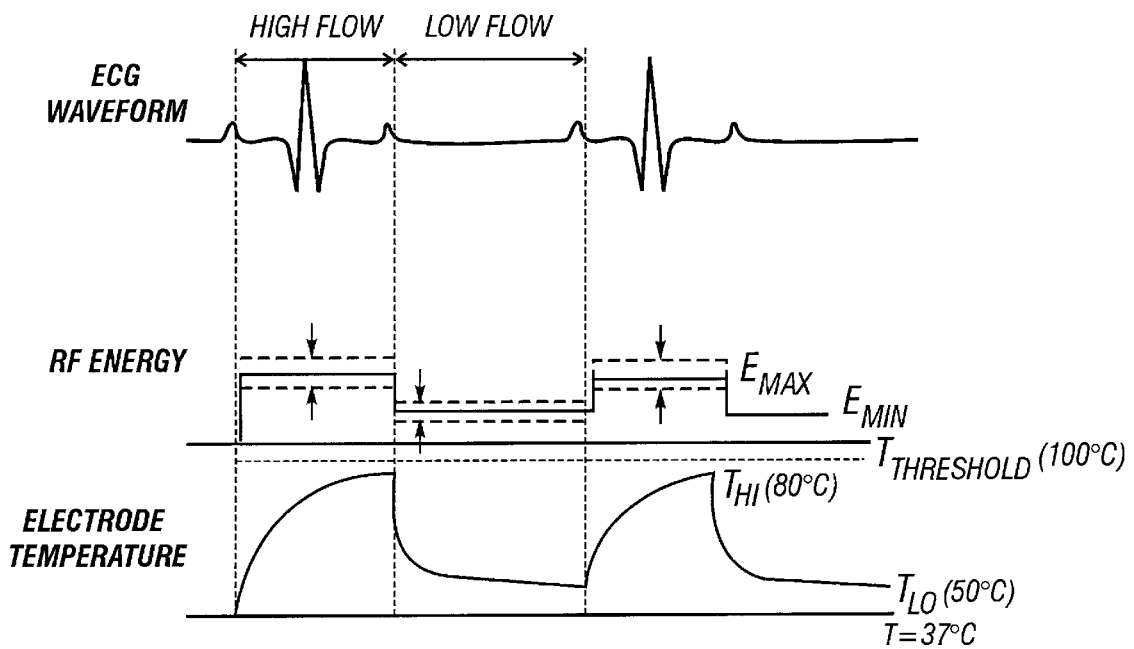
FIG. 11 is a graph depicting ECG waveforms during normal sinus rhythm (NSR), corresponding automatic temperature controlled RF energy applied during NSR and resultant electrode temperature, each depicted as a function of time.
Figure 12:
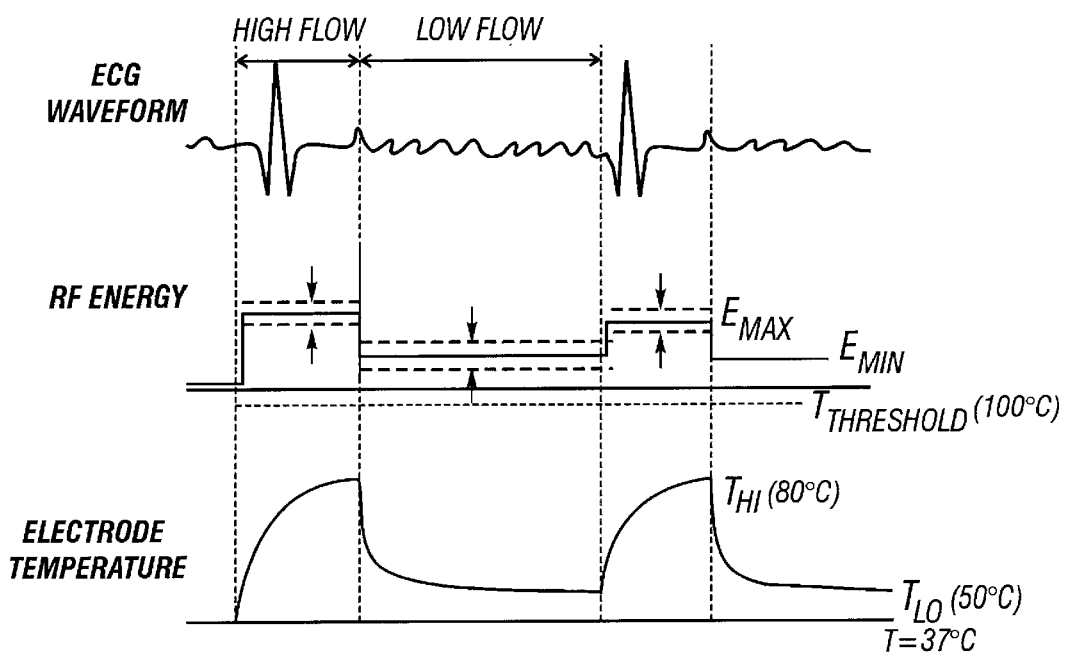
FIG. 12 is a graph depicting ECG waveforms during atrial fibrillation (AF), corresponding automatic temperature controlled RF energy applied during AF and resultant electrode temperature, each depicted as a function of time.

As shown in FIGS. 11 and 12, at the beginning of a high flow rate period, the RF energy level is pulsed up from the minimum value, e.g., zero, to the maximum value which is greater than the minimum value. At the end of the high flow rate period, the RF energy is pulsed down to the minimum value. The energy remains at this level throughout the low flow rate period, until the start of the next high flow rate period, at which time the RF energy is again pulsed up to the maximum value.

As indicated by the electrode-temperature-verses-time curve, during high flow rate periods, when RF energy of a first level is applied to the electrode, the temperature of the electrode approaches the high target temperature. As previously mentioned, the system provides temperature feedback signals to the PCS microprocessor. The PCS microprocessor monitors the temperature of the electrode and is adapted to control the RF generator such that the RF energy provided by the RF generator allows the electrode temperature to approach the high target temperature without exceeding the threshold maximum temperature. If the high target temperature is not reached during the first high fluid-flow period, the PCS microprocessor may incrementally increase the RF energy during subsequent high fluid-flow periods, as indicated by the dashed lines on the RF energy graph, until the high target temperature is reached. Likewise, if the electrode temperature exceeds the high target temperature but is less than the threshold maximum temperature, the PCS microprocessor may incrementally decrease the RF energy during subsequent high fluid-flow periods. If the threshold maximum value is exceeded, the PCS microprocessor shuts down the RF generator.

With continued reference to the electrode-temperature-verses-time curve of FIGS. 11 and 12, during low flow rate periods, when RF energy of a second level is applied to the electrode, the temperature of the electrode approaches a low target temperature, which is preferably 50° C. If the temperature of the electrode does not decrease toward the low target temperature sufficiently fast, the PCS microprocessor may incrementally decrease the RF energy during subsequent low fluid-flow periods, as indicated by the dashed lines in the RF energy graph, until the low target temperature is reached. Conversely, if at anytime during a low flow rate period the electrode temperature decreases to a level less than the low target temperature, the PCS microprocessor may incrementally increase the RF energy during subsequent low fluid-flow periods to maintain the electrode temperature at or near the low target temperature.

Figures 1, 13:
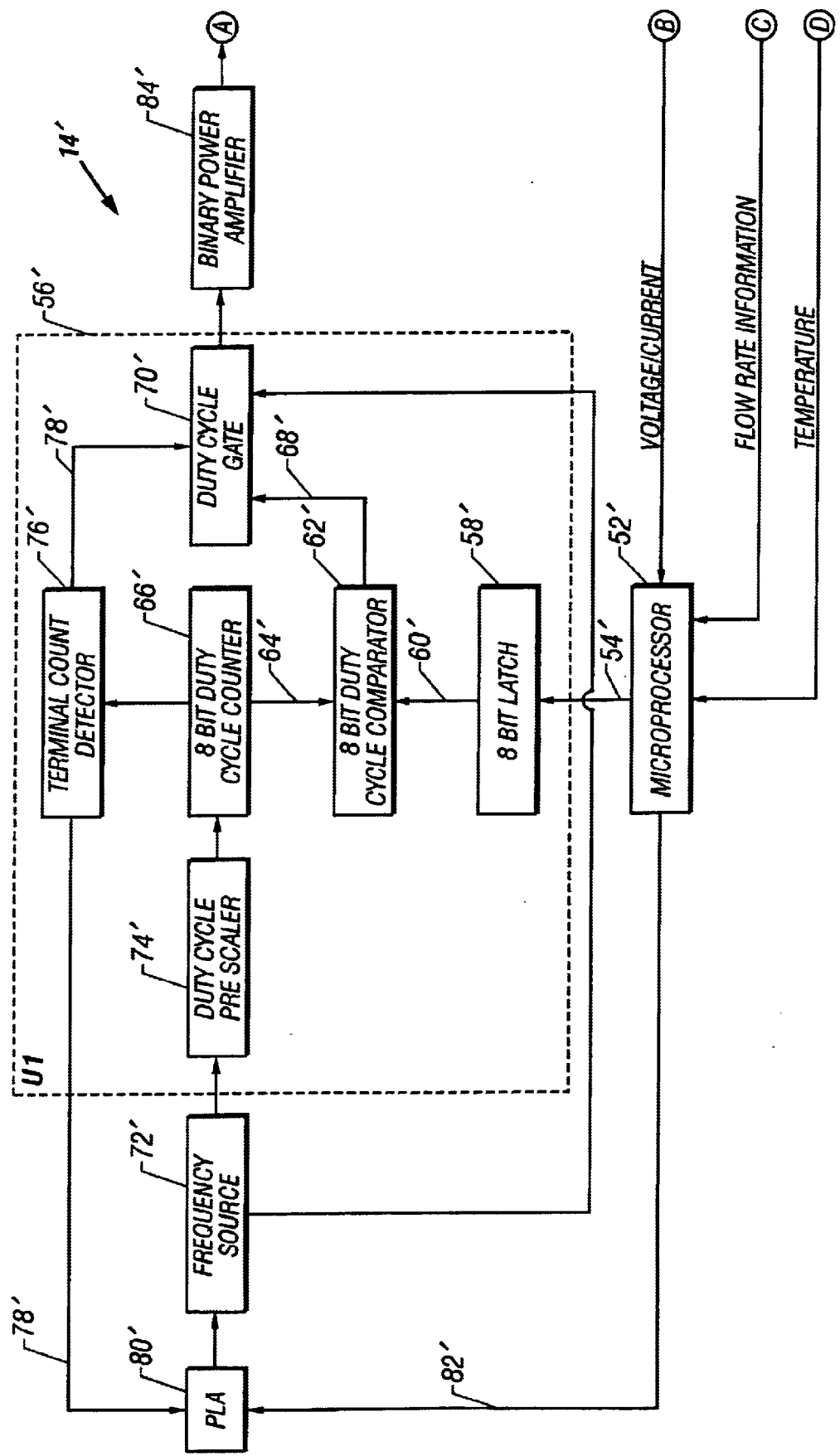
Figures 2, 13:
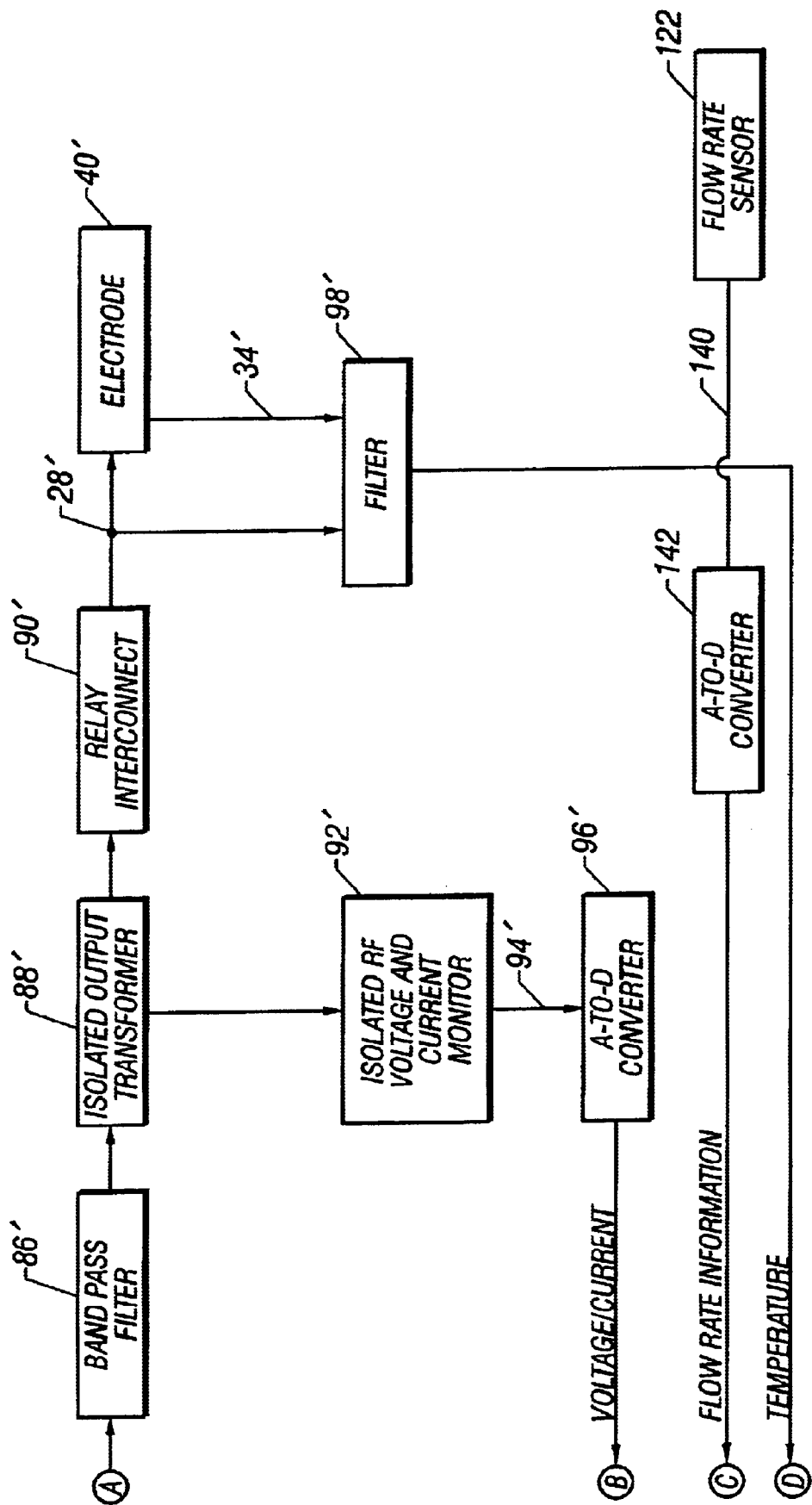

With reference to FIGS. 13-1 and 13-2, there is shown a block diagram of a flow sensor embodiment of an ablation system which incorporates aspects of the invention. Except for the use of a flow sensor, instead of an ECG device, as a means of obtaining flow rate information, the ablation system of FIGS. 13-1 and 13-2 is generally similar to the ablation system of FIGS. 4A and 4B. For ease in correlating the two configurations, the numerals associated with elements of the second configuration are the same as those of the first configurations except they are primed. For numerals that are not primed there is no correlating element in the first configuration. Because of the similarity between the two configurations, a description of the common elements is not repeated.

Similar to the previous configuration, this ablation system includes a single channel power control system 14' for use with a catheter system having a single band electrode 40'. As will be discussed in relation to other figures, an ablation system may include a multi-channel power control system 14' for use with a catheter system having a plurality of flow sensors 122 and band electrodes 40'.

With reference to FIG. 13-2, a flow sensor 122 provides flow rate information to the PCS microprocessor 52'. The flow sensor 122 may be any device capable of sensing the flow of fluid and providing an electrical signal based on the sensation of fluid flow. In one embodiment of the invention, the flow sensor 122 is an anemometer, preferably a hot wire anemometer comprising three perpendicular 500 $\mu$m×5 $\mu$m×2 $\mu$m polysilicon hot-wires that provide fluid flow measurements with time constants in the range of 120 and 330 $\mu$seconds, such as described in "Three dimensional silicon triple-hot-wire anemometer based on polymide joints", Thorbjorn Ebefors, Edvard Kalvesten, and Goran Stemme, IEEE Int. workshop on Micro Electro Machined System (MEMS 1998), Heidelberg, Germany, Jan. 25–29, 1998. In other embodiments, the flow sensor may be the feedback from a Doppler ultrasound machine such as those manufactured by Acuson (models Sequoia and Apsen). The output 140 of the flow rate sensor 122 passes through and an analog-to-digital converter 142 and is then fed to the PCS microprocessor 52'.

Figure 14:
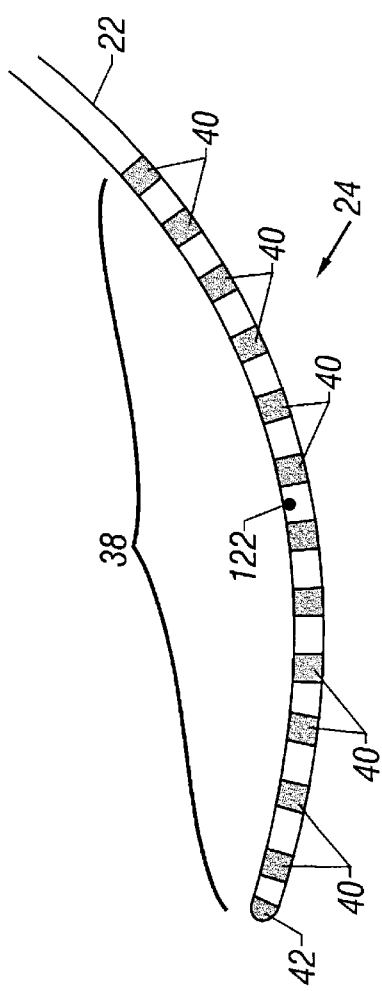
FIG. 14 is a diagram of the distal end segment of the catheter system of FIG. 2 showing a single flow sensor positioned between two adjacent band electrodes.
Figure 15:
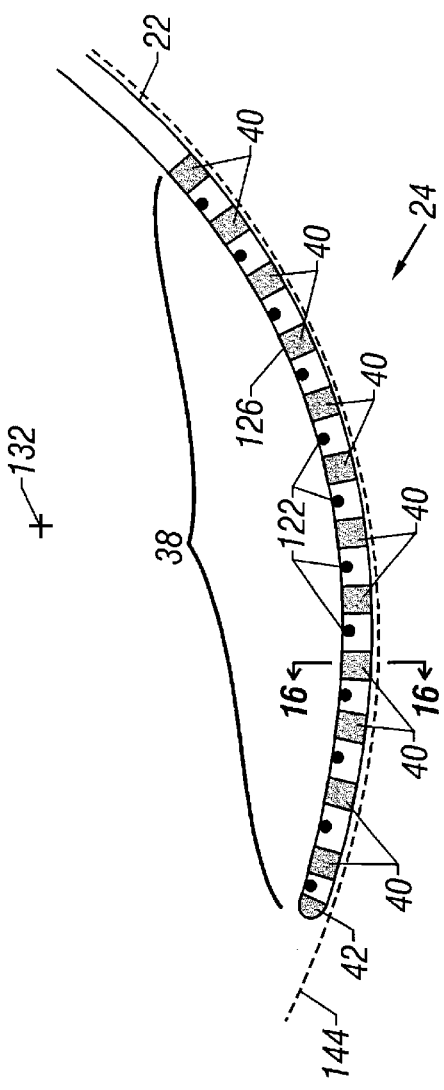
FIG. 15 is a diagram of the distal segment of the catheter system of FIG. 2 showing a plurality of flow sensors positioned along the length of the distal segment, each between a pair of adjacent band electrodes.

As shown in FIGS. 14 and 15, one or more flow sensors 122 may be positioned along the distal segment 24 of the catheter. In FIG. 14, a single flow sensor 122 is positioned near the center of the electrode system 38, between a pair of adjacent band electrodes 40. In this arrangement, the flow sensor 122 is located between the two middle electrodes 40 such that the biological fluid flow measurement is representative of the flow rate along the entire electrode system 138. This single flow sensor 122 provides flow rate information to the PCS microprocessor that is used to control the energy application to each band electrode 40.

In another arrangement, as shown in FIG. 15, a plurality of flow sensors 122 are positioned at various points along the length of the electrode system 38. The flow sensors 122 may be embedded in the catheter shaft 22 between pairs of adjacent electrodes 40. Alternatively, the flow sensors 122 may be embedded in the electrodes 40. In the multiple flow sensor embodiment, each of the electrodes 40 has a flow sensor 122 associated with it and the energy applied to each electrode is individually controlled based on the flow rate information provided by its flow sensor.

Figure 16:
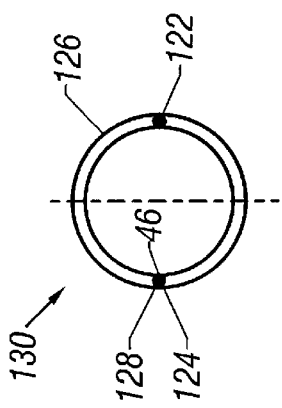
FIG. 16 is a cross-sectional view of the distal segment of FIG. 15 taken along line 16—16, depicting the position of a flow sensor on the inner radius of curvature.

As shown in FIGS. 15 and 16, the distal region 24 of the deflected catheter shaft 22, has an outside radius of curvature 124 and an inside radius of curvature 126. The outside radius of curvature 124 is defined by the longitudinal line 144 positioned at the outer most point 128 of the outer half 130 of the catheter, most distant from a reference center point 132 of the catheter distal tip 134 curve. In FIG. 15, the longitudinal line 144 is shown slightly removed from the catheter shaft 22 in order to more clearly identify the outside radius of curvature. During ablation procedures, it is intended that the outside radius of curvature 124 contact the biological tissue undergoing ablation and that the inside radius of curvature be in the blood pool. As shown in FIG. 16, the flow sensor 122 is located on the inside radius of curvature 126 thereby placing it within the blood pool, while thermal sensors 46 are located on the outside radius of curvature.

Figure 17:
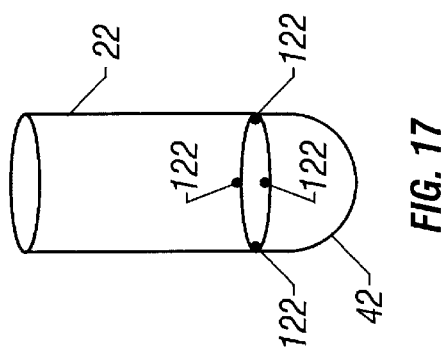
FIG. 17 is a schematic diagram of the tip electrode of the catheter system of FIG. 2 showing a plurality of flow sensors positioned around the perimeter of the electrode.

In other catheter systems with tip ablating electrodes, such as shown in FIG. 17, one or more flow sensors 122 may be associated with the tip electrode 42. The flow sensors 122 are embedded near or on the surface of the electrode. In the case of multiple flow sensors 122, the PCS microprocessor may control the application of energy based on the lowest of all flow rates measured or possibly the average flow rate.

Figure 18A:
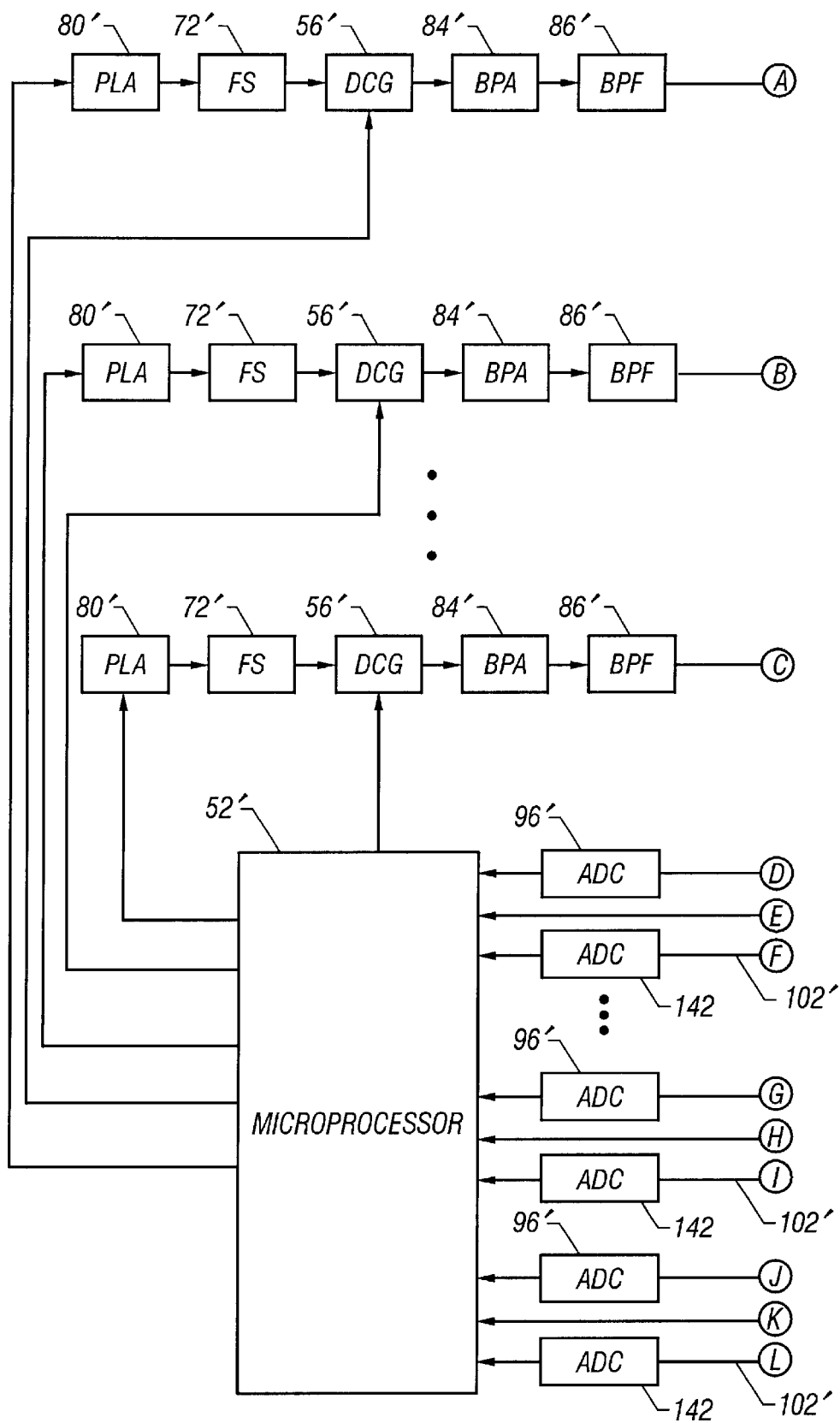
FIGS. 18A and 18B form a block diagram of a multi-channel ablation system configured in accordance with the configuration of FIGS. 13-1 and 13-2 wherein a single PCS microprocessor controls the application of ablation energy to each channel individually based in part on fluid-flow rate information provided by a plurality of flow sensors.
Figure 18B:
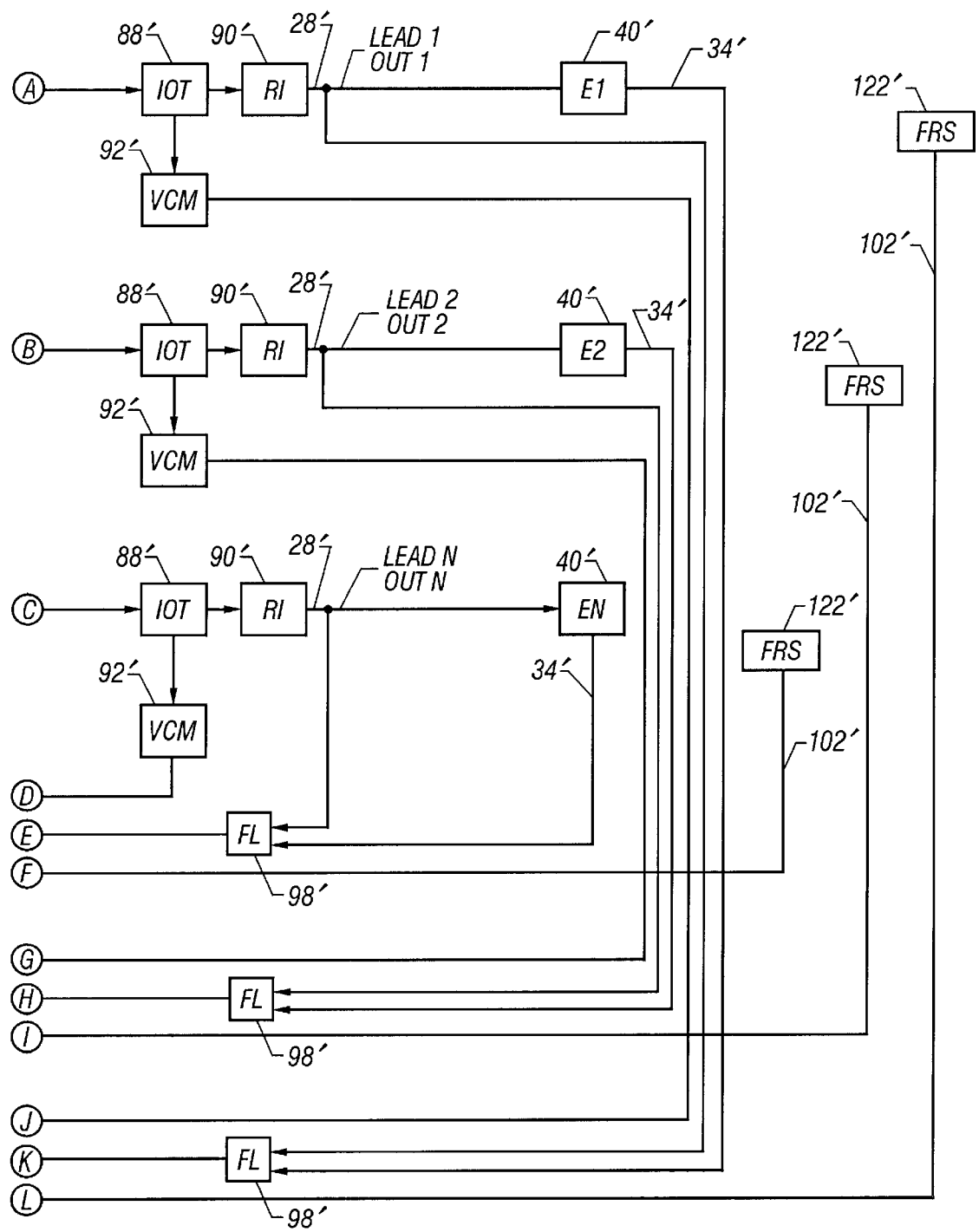

Referring now to FIGS. 18A and 18B, a block diagram of a multi-channel ablation system with flow sensors for use with a catheter system having a plurality of ablation electrodes 40' is shown. Although only three complete channels are shown, the system comprises many more as indicated by the successive dots. Those channels are not shown in FIGS. 18A and 18B to preserve clarity of illustration.

The single PCS microprocessor 52', which again is part of the controller 30 (FIG. 1), controls the duty cycle and the phase of each channel individually in this embodiment. Each channel shown comprises the same elements and each channel produces its own power output signal 28' (OUT1, OUT2, through OUTn where "n" is the total number of channels) on respective electrode leads (LEAD 1, LEAD 2, through LEAD n where "n" is the total number of leads).

The flow sensor embodiment described above has two primary modes of operation: a constant power mode and an automatic temperature control mode. Both modes of operation are very similar to the operation of the previously described ECG embodiment. The flow sensor embodiment of the system takes actual biological fluid flow measurements within the biological site, e.g., the heart, and delivers the signal to the PCS microprocessor for analysis.

Figure 19:
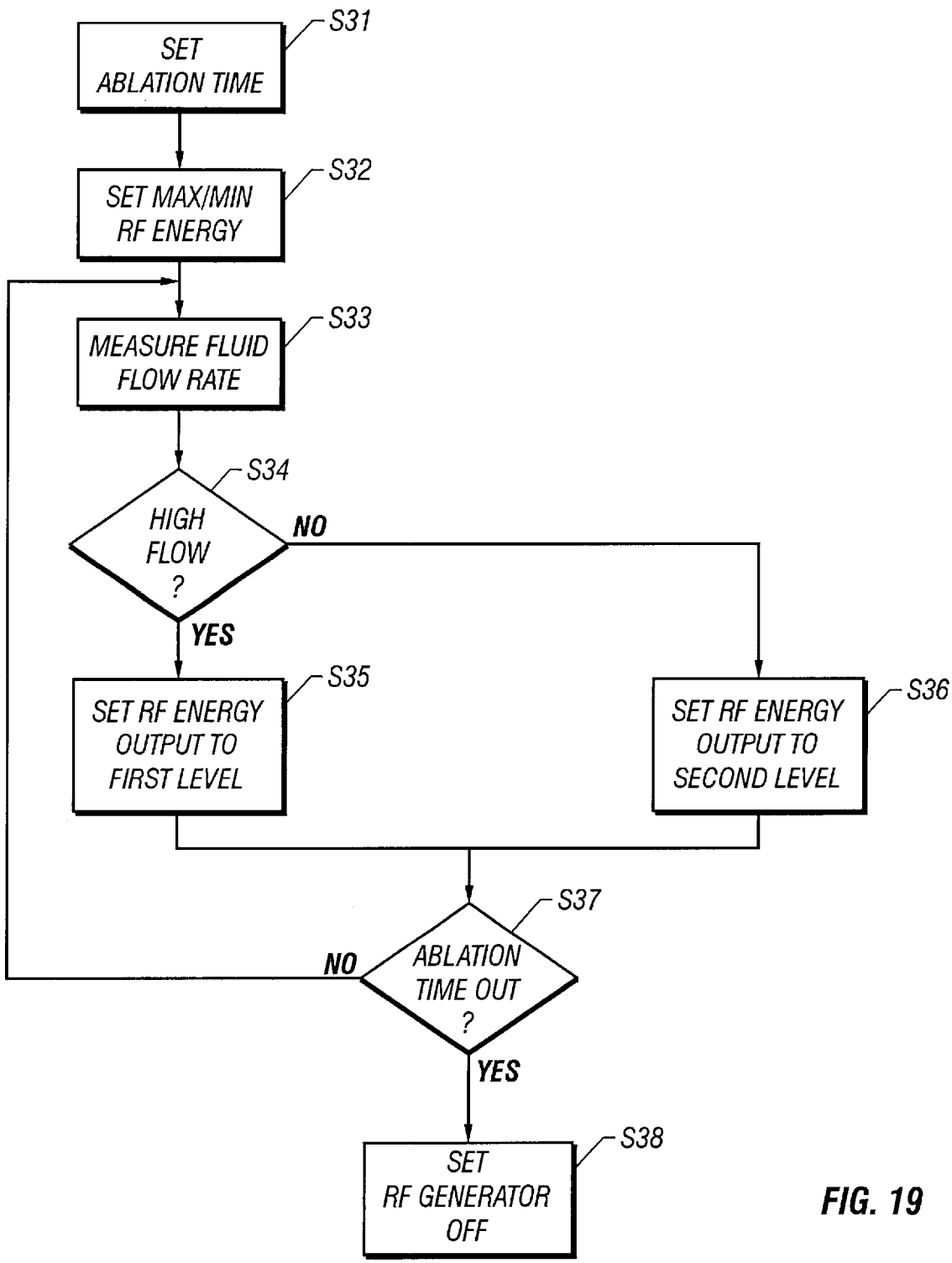
FIG. 19 is a flow chart of the operation of the flow sensor system of FIGS. 13-1 and 13-2 when in a constant power mode.

With reference to FIG. 19, when operating in the constant power mode, at step S31, the user sets an ablation time and, at step S32 a maximum RF energy level value and a minimum RF energy level value which is less than the maximum value. Again, these values are selected by the user based on various factors, including the biological site being ablated, the location of the ablation area within the biological site, the thermal, electrical and optical properties of the tissue being ablated, the degree of contact between the electrode and the tissue and the desired characteristics of the ablation lesion desired, i.e., size and depth of lesion.

At step S33, one or more flow sensors carried by the catheter measure the biological fluid-flow rate and send flow-rate-information signals to the PCS microprocessor for analysis. The PCS microprocessor is programmed to convert the flow-rate-information signals into fluid flow rate or fluid velocity values. The PCS microprocessor is further programmed to identify the measured velocity values as being either "high" or "low." The PCS microprocessor does this by comparing the measured velocity value to a predetermined velocity value. Measured velocity values greater than or equal to the predetermined velocity value are considered "high", while measured velocity values less than the predetermined velocity value are considered "low." In one configuration, the flow rate of biological fluid through the site being treated is monitored using the flow rate sensors prior to ablation for a time period sufficient to identify a high-flow rate/low-flow rate pattern. The flow rate pattern is then analyzed by the PCS microprocessor to identify high fluid flow and low fluid flow rates and to define the predetermined velocity value based on the high and low flow rates. For example, if the average high fluid flow rate within the time period is 30 cm/second and the average low fluid flow rate is 20 cm/second, the PCS microprocessor may identify the predetermined velocity value as the average of the two, i.e., 25 cm/second. Thus periods during which the measured velocity value is greater than or equal to 25 cm/second would be considered high fluid-flow periods and those periods during which the measured velocity value is less than 25 cm/second would be considered low fluid-flow periods. Alternatively, the user may monitor the flow rate pattern and, using his personal judgment, manually program the predetermined velocity value into the PCS microprocessor through front panel controls on the RF generator based. In an alternate configuration, the PCS microprocessor may comprise a look up table that correlates user entered parameters with predetermined velocity values. Such parameter may include the biological site being ablated, the location of the ablation area within the biological site and the physical characteristics of the patient being treated.

At step S34, the PCS microprocessor determines whether the flow rate is high or low. If the flow rate is high, at step S35 the PCS microprocessor controls the output of RF energy from the RF generator such that RF energy of a first level is applied to the electrode. This first level of energy is substantially equal to the maximum RF energy level selected by the user. If the flow rate is low, at step S36 the PCS microprocessor controls the output of RF energy from the RF generator such that RF energy of a second level is applied to the electrode. This second level of energy is substantially equal to the minimum RF energy level selected by the user and is usually at or near zero.

At step S37, the PCS microprocessor determines whether the ablation time has expired. If the time has not expired, the operation process continues to measure the fluid-flow rate (step S33). If the ablation time has expired, the PCS microprocessor sets the RF generator off at step S38.

Detailed operations of the constant power mode of the flow sensor embodiment, and the characteristics of the applied RF energy and the corresponding electrode-temperature-versus-time curves that occur during operation are similar to those described with regard to the ECG embodiment, as shown in FIGS. 8 and 9. Accordingly, a description of these characteristics is not repeated.

Figure 20:
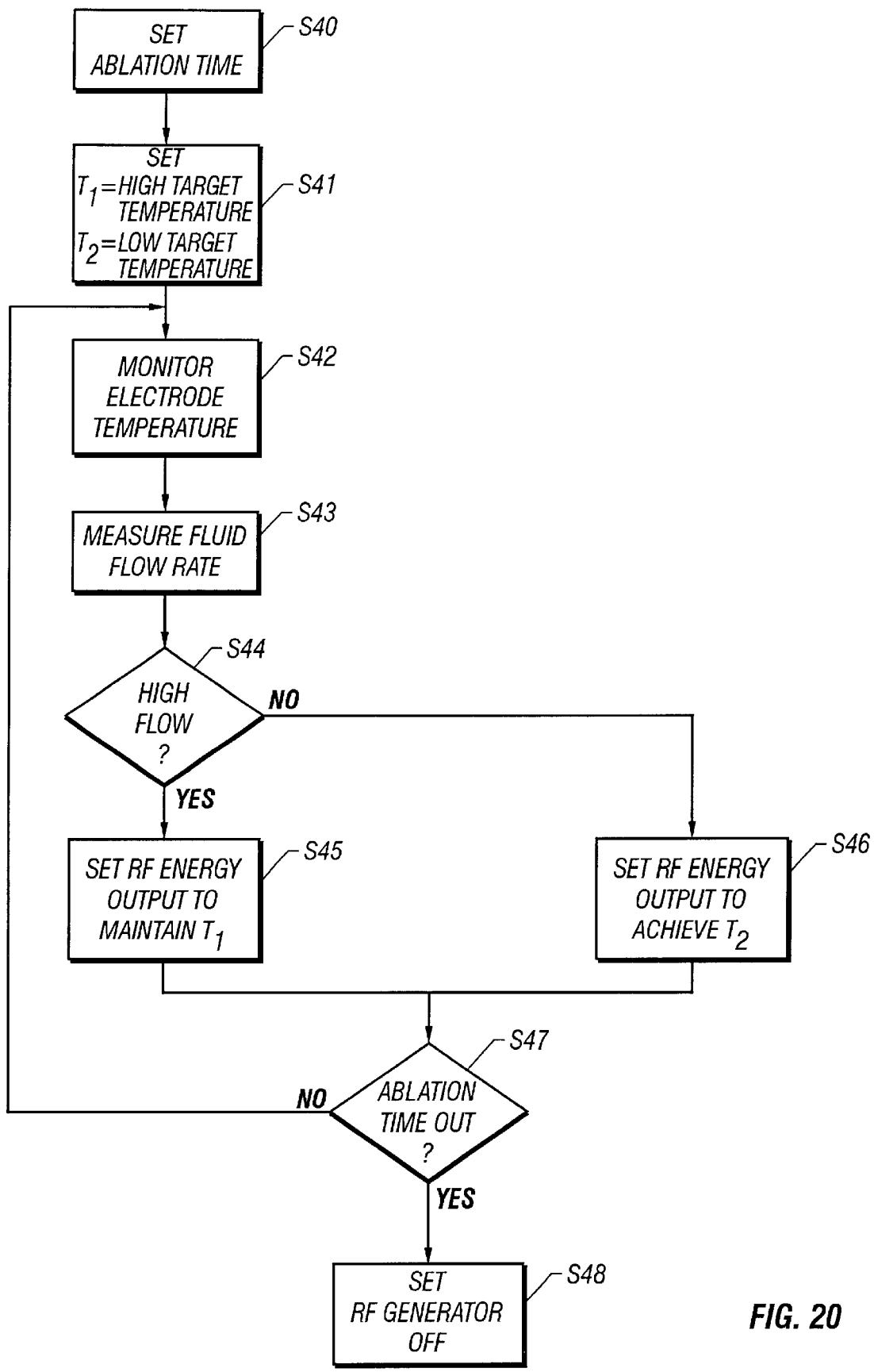
FIG. 20 is a flow chart of the operation of the flow sensor system of FIGS. 13-1 and 13-2 when in the automatic temperature controlled mode.

With reference to FIG. 20, when operating in the automatic temperature control mode, at step S40, the user sets an ablation time and, at step S41 a high target temperature and a low target temperature. Again, these values are selected by the user based on various factors, including the biological site being ablated, the location of the ablation area within the biological site, the thermal, electrical and optical properties of the tissue being ablated, the degree of contact between the electrode and the tissue and the desired characteristics of the ablation lesion desired, i.e., size and depth of lesion. The temperature and time values may be set through front panel controls of the RF generator.

At step S42, the PCS microprocessor monitors the electrode temperature using the temperature feedback signals provided by the thermal sensor on the electrode. At step S43, one or more flow sensors carried by the catheter measure the biological fluid-flow rate and send flow-rate-information signals to the PCS microprocessor for analysis.

At step S44 the PCS microprocessor determines whether the actual measured flow rate is high or low. If the flow rate is high, at step S45 the PCS microprocessor controls the output of RF energy from the RF generator such that the RF energy provided to the electrode allows the electrode temperature to approach the high target temperature, without exceeding a threshold maximum temperature, which is approximately 100° C. If the threshold maximum temperature is exceeded, the PCS microprocessor shuts down the RF generator. If the flow rate is low, at steps S46 the PCS microprocessor controls the output of RF energy from the RF generator such that RF energy provided to the electrode allows the electrode temperature to approach the low target temperature.

At step S47, the PCS microprocessor determines whether the ablation time has expired. If the time has not expired, the operation process returns to step S42. If the ablation time has expired, the PCS microprocessor sets the RF generator off at step S48.

The PCS microprocessor is programmed to identify "high" and "low" flow rates accordingly, in the manner as previously discussed with regard to the constant power mode operation of the flow sensor embodiment. In addition, the characteristics of the applied RF energy and the electrode temperatures curves and the corresponding temperature feedback control operation, that occur during automatic temperature mode operation of the flow sensor embodiment are similar to those described with regard to the automatic temperature mode operation of the ECG embodiment, as shown in FIGS. 11 and 12. Accordingly, a description of these characteristics and operational features is not repeated.

In an alternate flow sensor embodiment, also having a constant power mode and an automatic temperature control mode, the PCS microprocessor is adapted to continuously monitor the fluid flow rate and to dynamically adjust the RF energy level provided by the generator by increasing or decreasing RF energy levels based on corresponding increases and decreases in fluid-flow rates.

Figure 21:
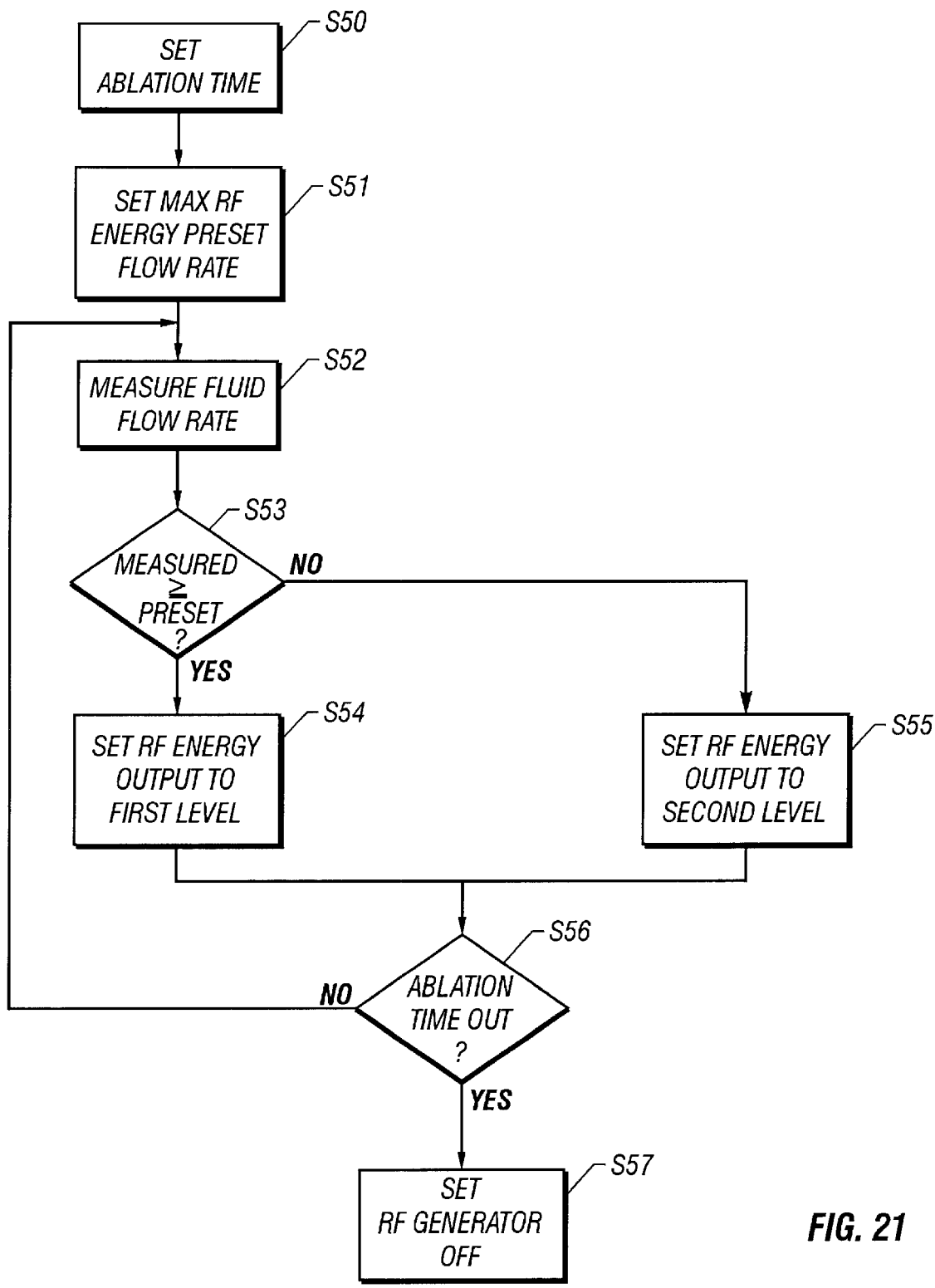
FIG. 21 is a flow chart of an alternate operation of the flow sensor system of FIGS. 13-1 and 13-2 when in a constant power mode.

With reference to FIG. 21, when operating this alternate flow sensor embodiment in the constant power mode, at step S50, the user sets an ablation time and, at step S51 a preset flow rate value and a maximum RF energy level value. These values may be selected and determined as described with reference to the previously discussed flow sensor embodiments. The ablation time, preset flow rate value and maximum RF energy level value may be set through front panel controls of the RF generator.

At step S52, one or more flow sensors carried by the catheter measure the biological fluid-flow rate and send flow-rate-information signals to the PCS microprocessor for analysis. At steps S53 the PCS microprocessor determines whether the measured flow rate is greater than or equal to the preset flow rate value. If the measured flow rate is greater than or equal to the preset flow rate value, at step S54 the PCS microprocessor controls the output of RF energy from the RF generator such that the maximum level of RF energy is applied to the electrode.

If the measured flow rate is less than the preset flow rate, at step S55 the PCS microprocessor calculates a rate of reduction for the flow rate. This rate of reduction is calculated by comparing the measured flow rate to the preset flow rate. In a preferred embodiment, the ratio of the two flow rates provides the comparison necessary to determine the rate of reduction. Using the rate of reduction in the flow rate, the PCS microprocessor determines a corresponding rate of reduction in the applied energy level. The correlation between reduction in the flow rate and the energy delivery rate can be a linear relationship, e.g., 1:1, 2:1, etc. Alternatively, the rate of decrease of energy delivery may be a polynomial of the inverse of the rate of flow decrease.

At step S56, the PCS microprocessor determines whether the ablation time has expired. If the time has not expired, the operation process returns to step S52. If the ablation time has been expired, the PCS microprocessor sets the RF generator off at step S57.

As with the previously discussed embodiments, the PCS microprocessor monitors the temperature of the electrode and is adapted to ensure that the RF energy provided by the RF generator is allowed to approach the maximum RF energy without exceeding a threshold maximum temperature value. If the threshold maximum value is exceeded, the PCS microprocessor shuts down the RF generator.

Figure 22:
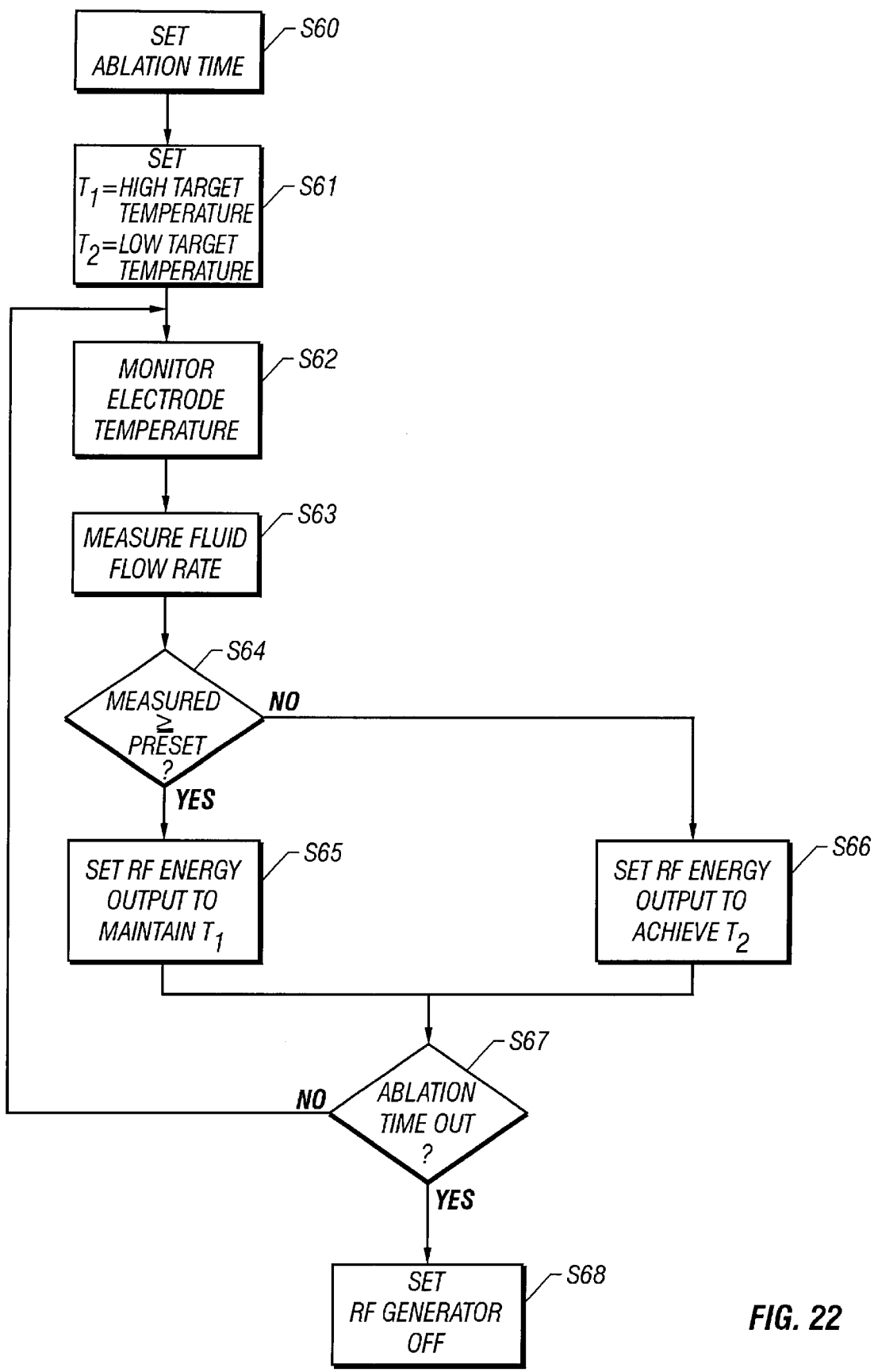
FIG. 22 is a flow chart of an alternate operation of the flow sensor system of FIGS. 13-1 and 13-2 when in the automatic temperature controlled mode.

With reference to FIG. 22, when operating the alternate flow sensor embodiment in the automatic temperature control mode, at step S60, the user sets an ablation time and, at step S61, a high target temperature, a low target temperature, and a preset flow rate. The target temperatures are selected in a manner similar to that previously discussed with respect to FIGS. 10 and 20, while the preset flow rate is selected in a manner similar to that previously discussed with regard to the other flow sensor embodiments. The temperature, time, and preset flow rate value may be set through front panel controls of the RF generator.

At step S62, the PCS microprocessor monitors the electrode temperature using the temperature feedback signals provided by the thermal sensor on the electrode. At step S63, one or more flow sensors carried by the catheter measure fluid-flow rate and send the flow-rate-information signals to the PCS microprocessor, where they are processed and compared to the preset flow rate.

At steps S64 the PCS microprocessor determines whether the measured flow rate is greater than or equal to the preset flow rate value. If the measured flow rate is greater than or equal to the preset flow rate value, at step S65 the PCS microprocessor calculates a rate of increase for the flow rate. This rate of increase is calculated by comparing the measured flow rate to the preset flow rate. In a preferred embodiment, the ratio of the two flow rates provides the comparison necessary to determine the rate of increase. Using the rate of increase in the flow rate, the PCS microprocessor determines a corresponding rate of increase in the applied energy level. The correlation between the increase in the flow rate and the energy delivery rate can be a linear relationship. Alternatively the rate of increase of energy delivery may be a polynomial of the inverse of the rate of flow increase.

During this process, the PCS microprocessor monitors the temperature of the electrode. The PCS microprocessor is adapted to control the RF generator such that the RF energy provided by the RF generator allows the electrode temperature to approach the high target temperature without exceeding the threshold maximum temperature. If the high target temperature is not obtained by the applied energy level, the PCS microprocessor may increase the RF energy until the high target temperature is reached. Likewise, if the electrode temperature exceeds the high target temperature but is less than the threshold maximum temperature, the PCS microprocessor may decrease the RF energy. If the threshold maximum value is exceeded, the PCS microprocessor shuts down the RF generator.

At steps S66, if the PCS microprocessor determines that the measured flow rate is less than the preset flow rate value, the PCS microprocessor calculates a rate of reduction for the flow rate. This rate of reduction is calculated by comparing the measured flow rate to the preset flow rate. In a preferred embodiment, the ratio of the two flow rates provides the comparison necessary to determine the rate of reduction. Using the rate of reduction in the flow rate, the PCS microprocessor determines a corresponding rate of reduction in the applied energy level. The correlation between reduction in the flow rate and the energy delivery rate can be a linear relationship. Alternatively, the rate of decrease of energy delivery may be a polynomial of the inverse of the rate of flow decrease.

During this process, the PCS microprocessor monitors the temperature of the electrode. If the temperature of the electrode does not decrease toward the low target temperature sufficiently fast, the PCS microprocessor may decrease the RF energy, until the low target temperature is reached. Conversely, if at anytime during a low flow rate period the electrode temperature decreases to a level less than the low target temperature, the PCS microprocessor may increase the RF energy to maintain the electrode temperature at or near the low target temperature.

At step S67, the PCS microprocessor determines whether the ablation time has expired. If the time has not expired, the operation process returns to step S62. If the ablation time has expired, the PCS microprocessor sets the RF generator off at step S68.

While the various embodiments of the invention have been described as using RF energy to effect ablation, the invention is not limited to this type of energy. Various other energy sources may be used such as microwave, ultrasound, laser and cyro sources.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A system for applying energy to biological tissue within a biological organ having fluid flowing therethrough, said system comprising:
 a generator for providing energy;
 a catheter carrying an electrode system at its distal end, the distal end adapted to be positioned in a biological organ and the electrode system adapted to receive energy from the generator;
 a device adapted to provide flow rate information indicative of the flow rate of the fluid through the biological organ; and
 a processor adapted to receive the flow rate information, process the flow rate information to assess whether the fluid-flow rate is high or low and control the generator such that the generator provides energy of a first level to the electrode during periods of high fluid-flow and energy of a second level, less than the first level, during periods of low fluid-flow.

2. The system of claim 1 wherein the processor is adapted to control the generator to increase the energy level to the first energy level at the beginning of the high flow period and to decrease the energy level to the second energy level toward the end of the high flow period and before the beginning of the next low flow period.

3. The system of claim 2 wherein the processor is adapted to increase the energy level by ramping up the energy level and to decrease the energy level by ramping down the energy level.

4. The system of claim 1 further comprising:
 a temperature sensor adapted to provide temperature signals to the processor, the signals indicative of the temperature at the electrode system;
 wherein the processor is adapted to determine the temperature at the electrode system based on the temperature signals and to control the generator such that the level of energy applied to the electrode system maintains the temperature of the electrode system at or near a target temperature.

5. The system of 4 wherein, during a sequence of alternating high flow rate periods and low flow rate periods, the processor is adapted to adjust the level of energy output by the generator during a subsequent low/high period based on the temperature of the electrode system during the previous low/high period.

6. The system of claim 4 wherein, during periods of high fluid-flow, the target temperature is a high target temperature and, during periods of low fluid-flow, the target temperature is a low target temperature, less than the high target temperature.

7. The system of claim 6 wherein the high target temperature is in the range between approximately 50° C. and approximately 100° C. and the low target temperature is in the range between approximately 37° C. and approximately 49.9° C.

8. The system of claim 1 further comprising:
 a temperature sensor is adapted to provide temperature signals to the processor, the signals indicative of the temperature at the electrode system;
 wherein the processor is adapted to determine the temperature at the electrode system based on the temperature signals and to control the generator such that the level of energy applied to the electrode system maintains the temperature of the electrode system below a maximum threshold temperature.

9. The system of claim 8 wherein the processor is adapted to shut off the generator when the temperature of the electrode system exceeds the maximum threshold temperature.

10. The system of claim 9 wherein the threshold temperature is 100° C.

11. The system of claim 1 wherein the flow rate information device comprises an electrocardiograph (ECG) device adapted to monitor changes in electrical activity and the flow rate information comprises ECG signals.

12. The system of claim 11 wherein the ECG device comprises at least one of an external ECG sensor.

13. The system of claim 11 wherein the ECG device comprises at least one of an internal ECG sensor.

14. The system of claim 11 wherein the ECG device comprises at least one ECG filter in electrical communication with the electrode system, the ECG filter adapted to receive electrical signals from the electrode system and output them as ECG signals.

15. The system of claim 14 wherein the electrode system comprises a single tip electrode.

16. The system of claim 14 wherein the electrode system comprises a plurality of band electrodes and the ECG device comprises a plurality of ECG filters, one in electrical communication with each of the band electrodes.

17. The system of claim 11 wherein, for an ECG signal providing a waveform having a sequence of alternating P waves and T waves, the processor is adapted to identify the periods between a P wave and its subsequent T wave as high fluid-flow periods and the periods between a T wave and the next P wave as low fluid-flow periods.

18. The system of claim 11 wherein, for an ECG signal providing a waveform having a sequence of alternating QRS complex waves and T waves, the processor is adapted to identify the periods between the onset of a QRS complex wave and the subsequent T wave as high fluid-flow periods and the periods between a T wave and the next QRS complex wave as low flow periods.

19. The system of claim 1 wherein the flow rate information device comprises at least one flow sensor located near the electrode system and adapted to sense fluid flow and the flow rate information comprises velocity values.

20. The system of claim 19 wherein the processor is adapted to identify periods during which the sensor signals provide a velocity value greater than or equal to a predetermined velocity value as high fluid-flow periods and those periods during which the velocity value is less than the predetermined velocity value as low fluid-flow periods.

21. The system of claim 20 wherein the electrode system comprises a tip electrode and the at least one flow sensor is at the surface of the tip electrode.

22. The system of claim 21 further comprising at least one additional flow sensor at the surface of the tip electrode at a distance from the other flow sensor;
 wherein the processor is adapted to control the energy provided by the generator based on the lowest velocity value.

23. The system of claim 19 wherein the electrode system comprises a plurality of band electrodes, the at least one flow sensor is at the outer surface of one of the band electrodes and the processor is adapted to control the energy provided by the generator to each of the electrodes based on the flow rate information provided by the at least one flow sensor.

24. The system of claim 23 wherein the band electrodes are arranged in a linear array and the at least one flow sensor is at the surface of one of the electrodes near the longitudinal center of the array.

25. The system of claim 19 wherein the electrode system comprises a plurality of band electrodes, the flow rate information devices comprises a plurality of flow sensors, one flow sensor associated with one band electrode and the processor is adapted to control the energy provided by the generator to each of the electrodes based on the flow rate information provided by the flow sensor associated with that electrode.

26. The system of claim 25 wherein the distal end of the catheter is precurved to have a radius of curvature comprising and inside portion and an outside portion and the flow sensor is positioned on the inside portion.

27. A method of applying energy to biological tissue within a biological organ, said method comprising the steps of:
 positioning an electrode within the biological organ, such that a portion of the electrode contacts the biological tissue;
 determining the biological fluid-flow rate within the biological organ;
 during periods of high biological fluid flow, applying energy of a first level to the biological tissue; and
 during periods of low biological fluid flow, reducing the level of energy applied to a second level, less than the first level.

28. The method of claim 27 wherein the first level of energy is substantially constant and the second level of energy is substantially zero.

29. The method of claim 27 wherein the steps of applying energy of a first level and reducing the level of energy to a second level comprises:
 increasing the energy to the first energy level at the beginning of a high flow period; and
 decreasing the energy level to the second energy level toward the end of the high flow period and before the low flow period.

30. The method of claim 29 wherein, other than during periods of increasing energy and decreasing energy, the first level of energy and the second level of energy are substantially constant.

31. The method of claim 27 further comprising:
 monitoring the temperature of the electrode; and
 adjusting the level of energy applied to the electrode to maintain the temperature of the electrode at or near a target temperature.

32. The method of claim 31 further comprising the step of, for a sequence of alternating high flow rate periods and low flow rate periods, adjusting the level of energy during a subsequent low/high period based on the temperature of the electrode during the previous low/high period.

33. The method of claim 31 wherein, during periods of high fluid-flow, the target temperature is a high target temperature and, during periods of low fluid-flow, the target temperature is a low target temperature, less than the high target temperature.

34. The system of claim 33 wherein the high target temperature is in the range between approximately 50° C. and approximately 100° C. and the low target temperature is in the range between approximately 37° C. and approximately 49.9° C.

35. The method of claim 27 further comprising the steps of:
 monitoring the temperature of the electrode; and
 adjusting the level of energy applied to the electrode to maintain the temperature of the electrode below a maximum threshold temperature.

36. The method of claim 35 wherein the maximum threshold temperature is approximately 100° C.

37. The method of claim 27 wherein the step of determining the biological fluid-flow rate comprises the steps of:
 measuring changes in voltage occurring in the human body with each heart beat to produce an electrocardiogram waveform having a sequence of alternating P waves and T waves; and
 identifying high fluid-flow periods as those periods between a P wave and its subsequent T wave and low fluid-flow periods are those periods between a T wave and the next P wave.

38. The method of claim 27 wherein the step of determining the biological fluid-flow rate comprises the steps of:
 measuring changes in voltage occurring in the human body with each heart beat to produce an electrocardiogram waveform having a sequence of alternating QRS complex waves and T waves; and
 identifying high fluid-flow periods as those periods between the onset of a QRS complex wave and the subsequent T wave and low fluid-flow periods are those periods between a T wave and the next QRS complex wave.

39. The method of claim 27 wherein the step of determining the biological fluid-flow rate comprises the steps of:
 measuring the velocity of the fluid flow; and
 identifying those periods during which the sensor signals provide a velocity value greater than or equal to a predetermined velocity value as high fluid-flow periods and those periods during which the velocity value is less than the predetermined velocity value as low fluid-flow periods.

40. A system for applying energy to biological tissue within a biological organ having fluid flowing therethrough, said system comprising:
 a generator for providing energy;
 a catheter carrying an electrode system at its distal end, the distal end adapted to be positioned in a biological organ and the electrode system adapted to receive energy from the generator;
 a device adapted to provide flow rate information indicative of the flow rate of the fluid through the biological organ; and
 a processor adapted to control the generator such that the generator provides energy to the electrode system in response to the fluid flow through the biological organ as indicated by the flow rate information, wherein a preset flow rate and a maximum energy level are programmed into the processor and the processor is adapted to:
 compare the measured flow rate to the preset flow rate;
 set the provided energy level to the maximum energy level when the measured flow rate is greater than or equal to the preset flow rate; and
 determine the rate of reduction of the measured flow rate relative to the preset flow rate and set the provided energy level to a value less than the maximum energy level, the provided level being a multiple of the maximum energy level, the multiple being set based on the determined reduction rate when the measured flow rate is less than the preset flow rate.

41. A system for applying energy to biological tissue within a biological organ having fluid flowing therethrough, said system comprising:
- a generator for providing energy;
- a catheter carrying an electrode system at its distal end, the distal end adapted to be positioned in a biological organ and the electrode system adapted to receive energy from the generator;
- a device adapted to provide flow rate information indicative of the flow rate of the fluid through the biological organ; and
- a processor adapted to control the generator such that the generator provides energy to the electrode system in response to the fluid flow through the biological organ as indicated by the flow rate information, wherein a preset flow rate, a high target temperature, and a low target temperature are programmed into the processor and the processor is adapted to:
  - monitor the temperature of the electrode;
  - compare the measured flow rate to the preset flow rate;
  - when the measured flow rate is greater than or equal to the preset flow rate,
    - determine the rate of increase of the measured flow rate relative to the preset flow rate;
    - set the applied energy level to a value greater than the current energy level, the applied level being a multiple of the current energy level, the multiple being set based on the determined increase rate;
    - compare the electrode temperature to the high target temperature;
    - adjust the applied energy level to maintain the electrode temperature near the high target temperature; and
  - when the measured flow rate is less than or equal to the preset flow rate,
    - determine the rate of reduction of the measured flow rate relative to the preset flow rate;
    - set the applied energy level to a value less than the current energy level, the applied level being a multiple of the current energy level, the multiple being set based on the determined reduction rate;
    - compare the electrode temperature to the low target temperature;
    - adjust the applied energy level to maintain the electrode temperature near the low target temperature.

42. A method of ablating biological tissue within a biological organ having biological fluid flowing therethrough, said method comprising:
- positioning an electrode within the biological organ such that a portion of the electrode contacts the biological tissue;
- measuring the biological fluid-flow rate within the biological organ; and
- applying energy to the electrode in response to the fluid-flow rate within the biological organ as indicated by the flow rate measurement, wherein
  - the step of measuring the biological fluid-flow rate comprises the steps of:
    - positioning a flow sensor within the biological fluid; and
    - determining the flow rate of the biological fluid; and
  - the step of applying energy to the electrode based on the flow rate measurement comprises the steps of:
    - establishing a preset flow rate and a maximum energy level;
    - comparing the measured flow rate to the preset flow rate;
    - when the measured flow rate is greater than or equal to the preset flow rate, setting the applied energy level to the maximum energy level; and
    - when the measured flow rate is less than the preset flow rate, determining the rate of reduction of the measured flow rate relative to the preset flow rate and setting the applied energy level to a value less than the maximum energy level, the applied level being a multiple of the maximum energy level, the multiple being set based on the determined reduction rate.

43. A method of ablating biological tissue within a biological organ having biological fluid flowing therethrough, said method comprising:
- positioning an electrode within the biological organ such that a portion of the electrode contacts the biological tissue;
- measuring the biological fluid-flow rate within the biological organ;
- applying energy to the electrode in response to the fluid-flow rate within the biological organ as indicated by the flow rate measurement;
- monitoring the temperature of the electrode; and
- adjusting the level of energy applied to the electrode to maintain the temperature of the electrode at or near a target temperature;
- wherein the steps of applying energy to the electrode based on the flow rate measurement and adjusting the level of energy applied to the electrode to maintain the temperature of the electrode at or near a target temperature comprise the steps of:
  - establishing a high target temperature, a low target temperature and a preset flow rate value;
  - monitoring the temperature of the electrode;
  - comparing the measured flow rate to the preset flow rate;
  - when the measured flow rate is greater than or equal to the preset flow rate,
    - determining the rate of increase of the measured flow rate;
    - setting the applied energy level to a value greater than the current energy level, the applied level being a multiple of the current energy level, the multiple being set based on the determined increase rate;
    - comparing the electrode temperature to the high target temperature;
    - adjusting the applied energy level to maintain the electrode temperature near the high target temperature; and
  - when the measured flow rate is less than or equal to the preset flow rate,
    - determining the rate of reduction of the measured flow rate;
    - setting the applied energy level to a value less than the current energy level, the applied level being a multiple of the current energy level, the multiple being set based on the determined reduction rate;
    - comparing the electrode temperature to the low target temperature;
    - adjusting the applied energy level to maintain the electrode temperature near the low target temperature.

44. The system of claim 43 wherein the high target temperature is in the range between approximately 50° C. and approximately 100° C. and the low target temperature is in the range between approximately 37° C. and approximately 49.9° C.

* * * * *